United States Patent [19]
Bender et al.

[11] Patent Number: 5,317,019
[45] Date of Patent: May 31, 1994

[54] INHIBITION OF INTERLEUKIN-1 AND TUMOR NECROSIS FACTOR PRODUCTION BY MONOCYTES AND/OR MACROPHAGES

[75] Inventors: Paul E. Bender, Cherry Hill, N.J.; Don E. Griswold, North Wales, Pa.; Nabil Hanna, Solana Beach, Calif.; John C. Lee, Radnor; Bartholomew J. Votta, Pottstown, all of Pa.; Philip L. Simon, Randolph, N.J.; Alison M. Badger, Bryn Mawr; Klaus M. Esser, Downingtown, both of Pa.

[73] Assignee: SmithKline Beecham Corp., Phildelphia, Pa.

[21] Appl. No.: 809,484

[22] PCT Filed: Jun. 12, 1990

[86] PCT No.: PCT/US90/03367
§ 371 Date: Dec. 12, 1991
§ 102(e) Date: Dec. 12, 1991

Related U.S. Application Data

[63] Continuation-in-part of Ser. No. 365,349, Jun. 13, 1989, abandoned.

[51] Int. Cl.$^5$ .................. A01N 43/40; A61K 31/54
[52] U.S. Cl. ...................... 514/224.2; 514/230.5; 514/258; 514/303; 514/333; 514/338; 514/339
[58] Field of Search ............. 546/271; 514/339, 333, 514/338, 224.2, 230.5, 258, 303

[56] References Cited

U.S. PATENT DOCUMENTS 4,794,114  12/1988  Bender et al. .................. 514/333

OTHER PUBLICATIONS

Chemical Abstracts, vol. 114, No. 21, Abstract 199,0806, p. 21, May 27, 1991.

*Primary Examiner*—C. Warren Ivy
*Assistant Examiner*—Raymond Covington
*Attorney, Agent, or Firm*—Dara L. Dinner; Stephen Venetianer; Edward T. Lentz

[57] ABSTRACT

A method of inhibiting the production of interleukin-1 by monocytes and/or macrophages in a human in need thereof which comprises administering to such a human an effective, interleukin-1 production inhibiting amount of a diaryl-substituted imidazole fused to a second heterocyclic ring containing a nitrogen bridgehead atom wherein said second ring may also contain sulfur, oxygen or an additional nitrogen atom, and may contain additional unsaturation.

This invention relates to a method of inhibiting the production of Tumor Necrosis Factor (TNF) by monocytes or macrophages in a human in need thereof which comprises administering to such mammal an effective, TNF production inhibiting amount of a compound of Formula (I) as described herein. The compounds of Formula (II) are generally described as diaryl-substituted imidazole fused to a second heterocyclic ring containing a nitrogen bridgehead wherein said ring may also contain sulfur, oxygen, or an additional nitrogen atom, and may contain additional unsaturation.

4 Claims, 4 Drawing Sheets

INHIBITION OF INTERLEUKIN-1 AND TUMOR NECROSIS FACTOR PRODUCTION BY MONOCYTES AND/OR MACROPHAGES

This application is a continuation-in-part of earlier U.S. application Ser. No. 07/365,349, filed Jun. 13, 1989, now abandoned.

BACKGROUND OF THE INVENTION

This invention relates to a method of inhibiting the production of interleukin-1 by monocytes and/or macrophages in a human in need thereof which comprises administering to such human an effective, interleukin-1 production inhibiting amount of a diaryl-substituted imidazole fused to a second heterocyclic ring containing a nitrogen bridgehead atom wherein said second ring may also contain sulfur, oxygen or an additional nitrogen atom, and may contain additional unsaturation.

This invention relates to a method of inhibiting the production of Tumor Necrosis Factor (TNF) by monocytes or macrophages in a mammal in need thereof which comprises administering to such mammal an effective, TNF production inhibiting amount of a compound of Formula (II) as described herein. The compounds of Formula (II) are generally described as diaryl-substituted imidazole fused to a second heterocyclic ring containing a nitrogen bridgehead wherein said ring may also contain sulfur, oxygen, or an additional nitrogen atom, and may contain additional unsaturation.

Lednicer, U.S. Pat. No. 3,455,924, issued Jul. 15, 1969, describes compounds of the formula:

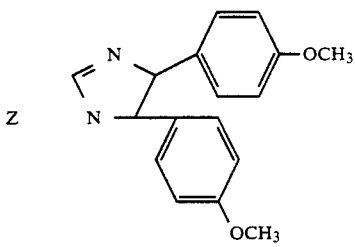

wherein Z is a bivalent radical selected from the group consisting of:

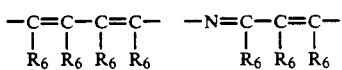

and

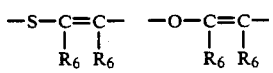

in which up to two of the parameters $R_1$, $R_2$, $R_3$ and $R_4$ are selected from the group consisting of hydrogen, lower alkyl and lower alkoxy having 1 to 4 carbon atoms, inclusive, hydroxy and nitro and the remaining parameters are hydrogen.

Adams et al., U.S. patent application Ser. No. 07/255,816, filed Oct. 11, 1988, generically discloses pyridyl substituted pyrrolo-[2,1-a]-imidazoles and pyridines as useful for inhibiting the 5-lipoxygenase pathway of arachadonic acid metabolism in an animal in need thereof. Specifically disclosed are the following compounds:

2-(4-methylthiophenyl)-3-(4-pyridyl)-6,7-dihydro-[5H]-pyrrolo-[1,2-a]-imidazole;
2-(4-methylsulfinylphenyl)-3-(4-pyridyl)-6,7,-dihydro-[5H]-pyrrolo[1,2-a]imidazole;
2-(4-ethylthiophenyl)-3-(4-pyridyl)-6,7-dihydro-[5H]-pyrrolo[1,2-a]imidazole;
2-(4-ethylsulfinylphenyl)-3-(4-pyridyl)-6,7-dihydro-[5H]-pyrrolo[1,2-a]imidazole;
2-(4-methylthiophenyl)-3-(4-(2-methyl)pyridyl)-6,7-dihydro-[5H]-pyrrolo[1,2-a]imidazole;
2-(4-methylsulfinylphenyl)-3-(4-(2-methyl)pyridyl)-6,7-dihydro-[5H]-pyrrolo[1,2-a]imidazole;
6-(4-methylthiophenyl)-5-(4-pyridyl)-2,3-dihydroimidazo[2,1-b]thiazole;
5-(4-methylthiophenyl)-6-(4-pyridyl)-2,3-dihydroimidazo[2,1-b]thiazole; and
3-(4-methylthiophenyl)-2-(4-pyridyl)-6,7-dihydro-[5H]-pyrrolo[1,2-a]imidazole.

Bender et al., U.S. Pat. No. 4,794,114, issued Dec. 27, 1988, disclose a method of inhibiting the production of IL-1 by monocytes and/or macrophages in a human in need thereof which comprises administering to such human an effective, interleukin-1 production inhibiting amount of a compound of the formula:

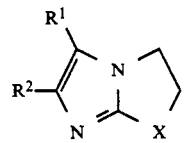

wherein:
One of $R^1$ and $R^2$ must be 4-pyridyl and the other is selected from monosubstituted phenyl wherein said substituent is selected from halo or $C_{1-4}$ alkoxy;
X is $CH_2$, $CH_2CH_2$ or $S(O)n$; and
n is 0, 1 or 2;
or a pharmaceutically acceptable salt thereof.

Dinarello et al., *Int. J. Immunopharmacology*, 6(1), 43–50 (1984), suggest that a product of arachidonate lipoxygenase is important in the sequence of events underlying cell activation for the production of human interleukin-1.

Griswold et al., *Inflammation*, 11(2), 189–199 (1987), discuss the inhibitory effects of 5-(4-pyridyl)-6(4-fluorophenyl)-2,3-dihydroimidazo-(2,1-b)thiazole and other dual inhibitors of arachidonic acid metabolism (i.e., inhibitors of 5-lipoxygenase and cyclooxygenase mediated arachidonate metabolism) on the edematous and cellular component of arachidonic acid-induced inflammation.

Lee et al., *Int. J. Immunopharmac.*, 10(7), 835–843 (1988), discuss that [5-(4-pyridyl)-6(4-fluorophenyl)-2,3-dihydroimidazo(2,1-b)thiazole], which inhibits both 5-lipoxygenase and cyclooxygenase-mediated arachidonate metabolism, was shown to be a potent inhibitor of IL-1 production by bacterial lipopolysaccharide (LPS)-stimulated human monocytes, and that other cyclooxygenase and/or 5-lipoxygenase inhibitors of arachidonic acid metabolism tested, with the exception of nordihydroguaiaretic acid, were inactive in inhibiting monocyte IL-1 production suggesting that the inhibition of IL-1 production by 5-(4-pyridyl)-6(4-fluorophenyl)-2,3-dihydroimidazo-(2,1-b)thiazole may be dissociated from its inhibition of fatty acid oxygenases.

There remains a need for compounds which are useful in inhibiting the production of interleukin-1 (IL-1)

by monocytes and/or macrophages in a human in need of such inhibition.

Studies have indicated that TNF is a glycoprotein and that its activity is associated with high molecular weight components. Mouse and rabbit TNF have been isolated, as has human TNF which sequence is taught in U.S. Pat. No. 4,879,226, issued Nov. 7, 1989. TNF is synthesized as a prohormone and subsequently cleaved at several sites to yield the mature hormone. While the active polypeptide itself has been evaluated for treatment of tumors due to its ealier reported antineoplastic activity, this administration has not been without may severe toxicities. Overproduction of TNF has further been implicated in the pathogenesis of endotoxin/septic shock, See e.g., Carswell et al., *Proc. Natl. Acad. Sci. USA*, 72, 3666–3670 (1975). Endotoxin is the lippolysaccharide component of the cell wall of gram-negative bacteria, and is a macrophage activator which induces the synthesis and secretion of cytokines and other biologically active molecules such as TNF. In sepsis, TNF production leads to hypotension, vascular endothelial permeability, and organ damage, i.e., some of the results of endotoxic shock. Adult Respiratory Distress Syndrome (ARDS) is frequently associated with sepsis and multiple organ failure which has led to the suggested role of TNF in the pathogenesis of ARDS. TNF is also the agent responsible for the weight loss (cachexia) found in chronic catabolic disease states, such as long term parasitic and viral infections and malignancies. This weight loss is a handicap to recovery and may even be fatal.

TNF also appears to play a role as an early product in the inflammatory response. See e.g., Old., *Nature*, 330, 602–03 (1987). It further appears that among the cytokines, while TNF production precedes and augments the function of IL-1 and other cytokines there is no clear data on how the relationship among these molecules contributes to inflammation-related disease states. TNF activates macrophages and enhances their cytotoxic potential in vitro. TNF has been shown to be chemotactic for monocytes, suggesting that the production of TNF at sites of injury may function to recruit additional macrophages and activate those macrophages already present.

Among the various mammalian conditions for which TNF is implicated in mediating or exacerbating rheumatoid arthritis, rheumatoid spondylitis, osteoarthritis, gouty arthritis and other arthritic conditions; sepsis, septic shock, endotoxic shock, gram negative sepsis, toxic shock syndrome, adult respiratory distress syndrome, fever and myalgias due to infection, such as influenza, cachexia secondary to infection or malignancy, cachexia secondary to acute immune deficiency syndrome (AIDS), keloid formation, scar tissue formation, Crohn's disease, uclerative colitis, or other inflammatory skin conditions such as pyresis.

The ability to control the adverse effects of TNF is furthered by the use of the compounds of this invention for humans who are in need of such use. There remains a need for compounds which are useful in inhibiting the production of tumor necrosis factor (TNF) by monocytes and/or macrophages in a human in need of such inhibition.

SUMMARY OF THE INVENTION

This invention relates to a method of inhibiting the production of interleukin-1 (IL-1) by monocytes and/or macrophages in a human in need thereof which comprises administering to such human an effective, IL-1 production inhibiting amount of a compound of the formula

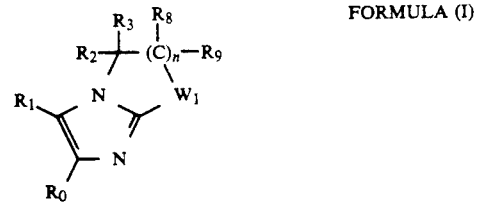

FORMULA (I)

wherein:

$W_1$ is $-(CR_4R_5)-(CR_6R_7)-$, $-CR_5=CR_7$, $-N=CR_7-$, $-S(O)_m-$ or $-O-$;

one of $R_1$ and $R_0$ is 4-pyridyl or $C_{1-4}$ alkyl-4-pyridyl, provided that when $R_1$ is $C_{1-4}$ alkyl-4-pyridyl the alkyl substituent is located at the 2-position of the pyridine ring, and the other of $R_1$ and $R_0$ is (a) phenyl or monosubstituted phenyl wherein said substituent is $C_{1-3}$ alkylthio, $C_{1-3}$ alkylsulfinyl, $C_{2-5}$ 1-alkenyl-1-thio, $C_{2-5}$ 1-alkenyl-1-sulfinyl, $C_{3-5}$ 2-alkenyl-1-thio, $C_{3-5}$ 2-alkenyl-1-sulfinyl, 1-acyloxy-1-alkylthio, $C_{1-2}$ alkoxy, halo, $C_{1-4}$ alkyl or Z wherein Z is $-S-S-Z_1$ and $Z_1$ is phenyl or $C_{1-9}$ alkyl; or (b) disubstituted phenyl wherein said substituent are, independently, $C_{1-3}$ alkylthio, $C_{1-2}$ alkoxy, halo or $C_{1-4}$ alkyl; or (c) disubstituted phenyl wherein one of said substituents is $C_{1-3}$ alkylsulfinyl, $C_{2-5}$ 1-alkenyl-1-thio, $C_{2-5}$ 1-alkenyl-1-sulfinyl, $C_{3-5}$ 2-alkenyl-1-thio, $C_{3-5}$ 2-alkenyl-1-sulfinyl or 1-acyloxy-1-alkylthio and the other is $C_{1-2}$ alkoxy, halo, or $C_{1-4}$ alkyl; or (d) disubstituted phenyl wherein the substituents are the same and are $C_{1-3}$ alkylsulfinyl, $C_{2-5}$ 1-alkenyl-1-thio, $C_{2-5}$ 1-alkenyl-1-sulfinyl, $C_{3-5}$ 2-alkenyl-1-thio, $C_{3-5}$ 2-alkenyl-1-sulfinyl or 1-acyloxy-1-alkylthio or wherein the substituents together form a methylene dioxy group; or (e) monosubstituted phenyl wherein said substituent is

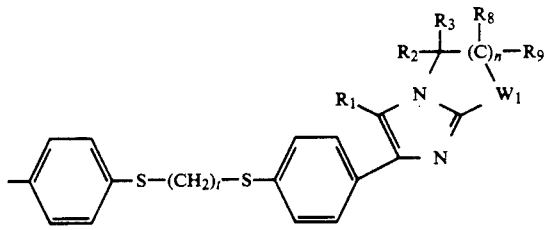

t is 0 or 1; $W_1$, $R_1$, $R_2$, $R_3$, $R_4$, $R_5$, $R_6$, $R_7$, $R_8$ and $R_9$ are as defined above;

provided that:

(1.) when $W_1$ is $-(CR_4R_5)-(CR_6R_7)-$ then n is 0 or 1;

and $R_2$, $R_3$, $R_4$, $R_5$, $R_6$, $R_7$, $R_8$, and $R_9$ are, independently, $-H$ or $C_{1-2}$ alkyl; and when $R_1$ or $R_0$ is 4-pyridyl, the other of $R_1$ and $R_0$ is other than mono-$C_{1-2}$ alkoxy-substituted phenyl or mono-halo-substituted phenyl; or when n is 0, $R_4$ and $R_5$ together are oxo; $R_4$ and $R_5$ are both fluoro, or one of $R_4$ and $R_5$ is H and the other is OH;

(2.) when $W_1$ is $-CR_5=CR_7-$ or $-N=CR_7-$ then
n is 1;
$R_3$, $R_5$, $R_7$ and $R_9$ are, independently, $-H$ or $C_{1-2}$ alkyl; and
$R_2$ and $R_8$ together represent a double bond in the B ring such that the B ring is an aromatic pyridine or pyrimidine ring;
(3.) when $W_1$ is $S(O)_m$ then
m is 0, 1 or 2;
n is 1 or 2; and
$R_3$ and $R_9$ are, independently, $-H$ or $C_{1-2}$ alkyl;
$R_2$ and $R_8$ are, independently, $-H$ or $C_{1-2}$ alkyl or $R_2$ and $R_8$ together represent a double bond in the B ring such that the B ring is an aromatic thiazole ring;
further provided that:
(a) when $R_2$ and $R_8$ are, independently, $-H$ or $C_{1-2}$ alkyl and $R_1$ or $R_0$ is 4-pyridyl, then the other of $R_1$ and $R_0$ is other than mono-$C_{1-2}$ alkoxy-substituted phenyl or mono-halo-substituted phenyl; and
(b) when $R_2$ and $R_8$ together represent a double bond in the B ring such that the B ring is an aromatic thiazole ring, then m is 0 and n is 1; and
(4) when $W_1$ is $-O-$ then
n is 1;
$R_3$ and $R_9$ are, independently, $-H$ or $C_{1-2}$ alkyl; and
$R_2$ and $R_8$ together represent a double bond in the B ring such that the B ring is an aromatic oxazole ring
or a pharmaceutically acceptable salt thereof.

This invention further relates to the intermediate compounds of Formulas C, D, E, F, If, and G.

This invention also relates to a method of inhibiting the production of tumor necrosis factor (TNF) by monocytes and/or macrophages in a human in need thereof which comprises administering to such human an effective, TNF production inhibiting amount of a compound of the Formula (II).

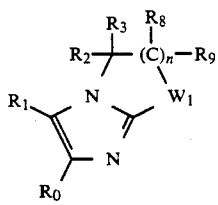

FORMULA (II)

wherein:
$W_1$ is $-(CR_4R_5)-(CR_6R_7)-$, $-CR_5=CR_7-$, $-N=CR_7-$, $-S(O)_m-$ or $-O-$;
one of $R_1$ and $R_0$ is 4-pyridyl or $C_{1-4}$ alkyl-4-pyridyl, provided that when $R_1$ is $C_{1-4}$ alkyl-4-pyridyl the alkyl substituent is located at the 2-position of the pyridine ring, and the other of $R_1$ and $R_0$ is
(a) phenyl or monosubstituted phenyl wherein said substituent is $C_{1-3}$ alkylthio, $C_{1-3}$ alkylsulfinyl, $C_{2-5}$ 1-alkenyl-1-thio, $C_{2-5}$ 1-alkenyl-1-sulfinyl, $C_{3-5}$ 2-alkenyl-1-thio, $C_{3-5}$ 2-alkenyl-1-sulfinyl, 1-acyloxy-1-alkylthio, $C_{1-2}$ alkoxy, halo, $C_{1-4}$ alkyl or Z wherein Z is $-S-S-Z_1$ and $Z_1$ is phenyl or $C_{1-9}$ alkyl; or
(b) disubstituted phenyl wherein said substitutes are, independently, $C_{1-3}$ alkylthio, $C_{1-2}$ alkoxy, halo or $C_{1-4}$ alkyl; or (c) disubstituted phenyl wherein one of said substituents is $C_{1-3}$ alkylsulfinyl, $C_{2-5}$ 1-alkenyl-1-thio, $C_{2-5}$ 1-alkenyl-1-sulfinyl, $C_{3-5}$ 2-alkenyl-1-thio, $C_{3-5}$ 2-alkenyl-1-sulfinyl or 1-acyloxy-1-alkylthio and the other is $C_{1-2}$ alkoxy, halo, or $C_{1-4}$ alkyl;
(d) disubstituted phenyl wherein the substituents are the same and are $C_{1-3}$ alkylsulfinyl, $C_{2-5}$ 1-alkenyl-1-thio, $C_{2-5}$ 1-alkenyl-1-sulfinyl, $C_{3-5}$ 2-alkenyl-1-thio, $C_{3-5}$ 2-alkenyl-1-sulfinyl or 1-acyloxy-1-alkylthio or wherein the substituents together form a methylene dioxy group; or
(e) monosubstituted phenyl wherein the substituent is

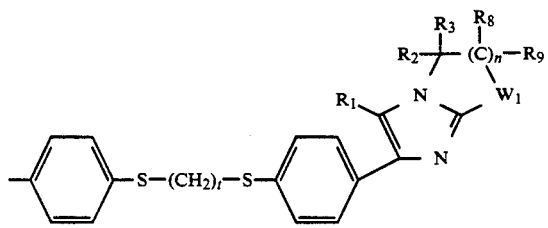

t is 0 or 1; $W_1$, $R_1$, $R_2$, $R_3$, $R_4$, $R_5$, $R_6$, $R_7$, $R_8$ and $R_9$ are as defined above;
provided that:
(1.) when $W_1$ is $-(CR_4R_5)-(CR_6R_7)-$ then
n is 0;
a) and $R_4$ and $R_5$ may together form an oxo; $R_4$ and $R_5$ are both flouro; or one of $R_4$ and $R_5$ is H and the other OH; or
(2.) when $W_1$ is $-CR_5=CR_7-$ or $-N=CR_7-$ then
n is 1;
$R_3$, $R_5$, $R_7$ and $R_9$ are, independently, $-H$ or $C_{1-2}$ alkyl; and
$R_2$ and $R_8$ together represent a double bond in the B ring such that the B ring is an aromatic pyridine or pyrimidine ring;
(3.) when $W_1$ is $S(O)_m$ then
m is 0, 1 or 2;
n is 1 or 2; and
$R_3$ and $R_9$ are, independently, $-H$ or $C_{1-2}$ alkyl;
$R_2$ and $R_8$ are, independently, $-H$ or $C_{1-2}$ alkyl or $R_2$ and $R_8$ together represent a double bond in the B ring such that the B ring is an aromatic thiazole ring; further provided that:
(a) when $R_2$ and $R_8$ are, independently, $-H$ or $C_{1-2}$ alkyl and $R_1$ or $R_0$ is 4-pyridyl, then the other of $R_1$ and $R_0$ mono-flouro-substituted phenyl; and
(b) when $R_2$ and $R_8$ together represent a double bond in the B ring such that the B ring is an aromatic thiazole ring, then m is 0 and n is 1; and
n is 1;
$R_3$ and $R_9$ are, independently, $-H$ or $C_{1-2}$ alkyl; and
$R_2$ and $R_8$ together represent a double bond in the B ring such that the B ring is an aromatic oxazole ring;
or a pharmaceutically acceptable salt thereof.

This invention also relates to a compound of Formula (IA) and the process of making a compound of Formula (IA):

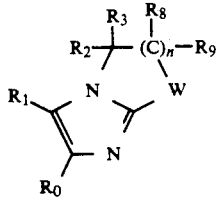

FORMULA (IA)

wherein:

W is —CR$_5$=CR$_7$—, —N=CR$_7$—, —S(O)$_m$— or —O—;

one of R$_1$ and R$_0$ is 4-pyridyl or C$_{1-4}$ alkyl4-pyridyl, provided that when R$_1$ is C$_{1-4}$ alkyl-4-pyridyl the alkyl substituent is located at the 2-position of the pyridine ring, and the other of R$_1$ and R$_0$ is
(a) monosubstituted phenyl wherein said substituent is C$_{1-3}$ alkylthio, C$_{1-3}$ alkylsulfinyl, C$_{2-5}$ 1-alkenyl-1-thio, C$_{2-5}$ 1-alkenyl-1-sulfinyl, C$_{3-5}$ 2-alkenyl-1-thio, C$_{3-5}$ 2-alkenyl-1-sulfinyl, 1-acyloxy-1-alkylthio, C$_{1-2}$ alkoxy, halo, C$_{1-4}$ alkyl, or Z wherein Z is —S—S—Z$_1$ and Z$_1$ is phenyl or C$_{1-9}$ alkyl; or
(b) disubstituted phenyl wherein said substituent are, independently, C$_{1-3}$alkylthio, C$_{1-2}$ alkoxy, halo or C$_{1-4}$ alkyl; or
(c) disubstituted phenyl wherein one of said substituents is C$_{1-3}$ alkylsulfinyl, C$_{2-5}$ 1-alkenyl-1-thio, C$_{2-5}$ 1-alkenyl-1-sulfinyl, C$_{3-5}$ 2-alkenyl-1-thio, C$_{3-5}$ 2-alkenyl-1-sulfinyl or 1-acyloxy-1-alkylthio and the other is C$_{1-2}$ alkoxy, halo, or C$_{1-4}$ alkyl;
(d) disubstituted phenyl wherein the substituents are the same and are C$_{1-3}$ alkylsulfinyl, C$_{2-5}$ 1-alkenyl-1-thio, C$_{2-5}$ 1-alkenyl-1-sulfinyl, C$_{3-5}$ 2-alkenyl-1-thio, C$_{3-5}$ 2-alkenyl-1-sulfinyl or 1-acyloxy-1 -alkylthio or wherein the substituents together form a methylene dioxy group; or
(e) monosubstituted phenyl wherein said substitutent is

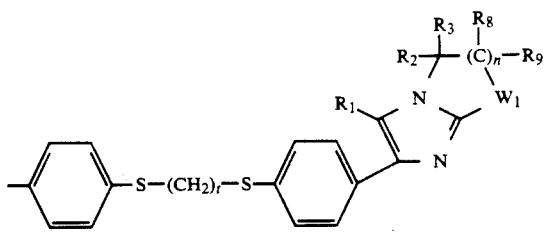

t is 0 or 1; W$_1$, R$_1$, R$_2$, R$_3$, R$_4$, R$_5$, R$_6$, R$_7$, R$_8$ and R$_9$ are as in Formula (I);

provided that:
(1.) when W is —CR$_5$=CR$_7$— or —N=CR$_7$— then
  n is 1;
  R$_3$, R$_5$, R$_7$ and R$_9$ are, independently, —H or C$_{1-2}$ alkyl;
  R$_2$ and R$_8$ together represent a double bond in the B ring such that the B ring is an aromatic pyridine or pyrimidine ring; and
(2.) when W is S(O)$_m$;
  m is 0, 1 or 2;
  n is 1 or 2;
  R$_3$ and R$_9$ are, independently, —H or C$_{1-2}$ alkyl; and R$_2$ and R$_8$ are, independently, —H or C$_{1-2}$ alkyl; then one of R$_1$ or R$_0$ is 4-pyridyl, and the other of R$_1$ and R$_0$ is:
  (a) monosubstituted phenyl wherein said substituent is selected from C$_{2-5}$ 1-alkenyl-1-thio, C$_{2-5}$ 1-alkenyl-1-sulfinyl, C$_{3-5}$ 2-alkenyl-1-thio, C$_{3-5}$ 2-alkenyl-1-sulfinyl, 1-acyloxy-1-alkylthio; or
  (b) disubstituted phenyl wherein said substituents are independently selected from C$_{1-3}$ alkylthio or halo; or
  (c) disubstituted phenyl wherein one of said substituents must be C$_{1-3}$ alkylthio, C$_{1-3}$ alkylsulfinyl, C$_{2-5}$ 1-alkenyl-1-thio, C$_{2-5}$ 1-alkenyl-1-sulfinyl, C$_{3-5}$ 2-alkenyl-1-thio, C$_{3-5}$ 2-alkenyl-1-sulfinyl or 1-acyloxy-1-alkylthio and the other is selected from C$_{1-2}$ alkoxy, halo or C$_{1-4}$ alkyl; and
(3.) when W is S(O)$_m$;
  m is 0;
  n is 1; and
  R$_2$ and R$_8$ together represent a double bond in the B ring such that the B ring is an aromatic thiazole ring; then
  R$_3$ and R$_9$ are, independently, —H or C$_{1-2}$ alkyl; and
(4.) when W is —O— then
  n is 1;
  R$_3$ and R$_9$ are, independently, —H or C$_{1-2}$ alkyl; and
  R$_2$ and R$_8$ together represent a double bond in the B ring such that the B ring is an aromatic oxazole ring; or or a pharmaceutically acceptable salt thereof.

This invention also relates to a pharmaceutical composition comprising an effective, non-toxic amount of a compound of Formula (IA) and a pharmaceutically acceptable carrier or diluent.

DETAILED DESCRIPTION OF THE INVENTION

Figure 1:
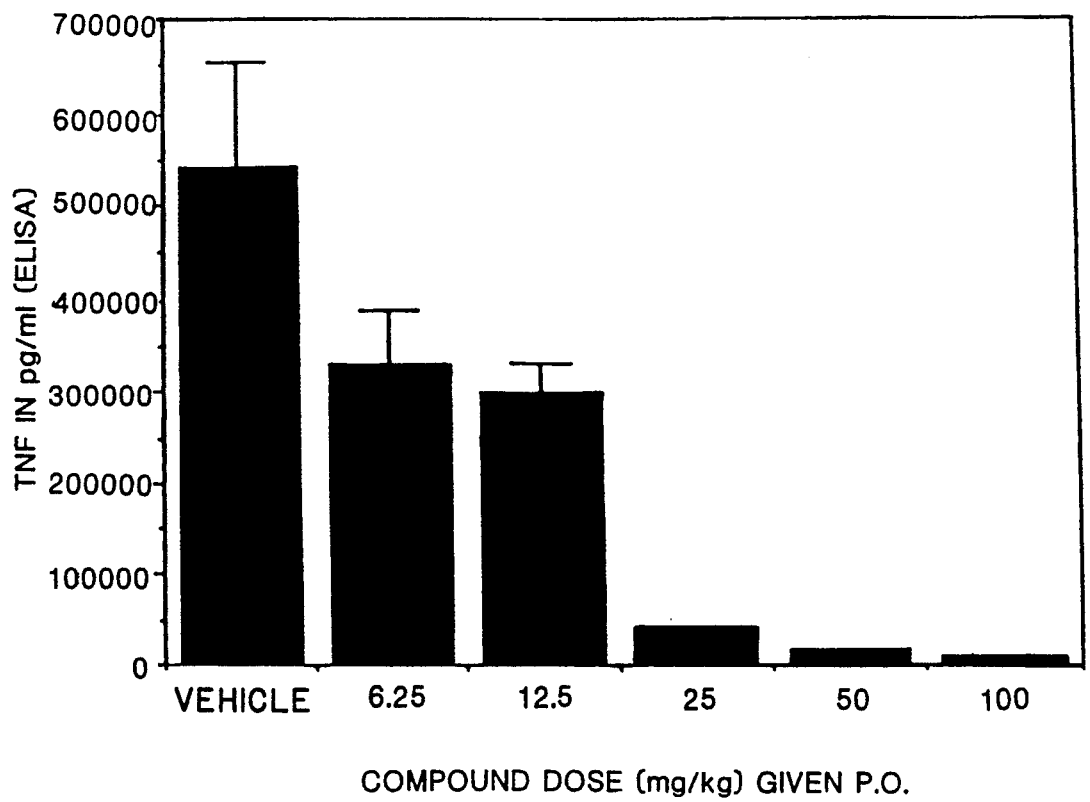

It will be apparent to one of skill in the art that all the compounds of Formula (IA) are embraced within the scope of the compounds of Formula (I). The compounds of Formula (I) are also embraced within the scope of the compounds of Formula (II). The compounds of Formula (I) differ from the compounds of Formula (II) wherein W$_1$ is —(CR$_4$R$_5$)—(CR$_6$R$_7$)— and when W$_1$ is S(O)$_m$ The compounds of Formula (II) do not have the following proviso language:
when W$_1$ is —(CR$_4$R$_5$)—(CR$_6$R$_7$)— then;
  n is 0 or 1;
  and R$_2$, R$_3$, R$_4$, R$_5$, R$_6$, R$_7$, R$_8$, and R$_9$ are, independently, —H or C$_{1-2}$ alkyl; and when R$_1$ or R$_0$ is 4-pyridyl, the other of R$_1$ and R$_0$ is other than mono-C$_{1-2}$ alkoxy-substituted phenyl or mono-halo-substituted phenyl; or
when W$_1$ is S(O)$_m$ then
  m is 0, 1 or 2;
  n is 1 or 2; and
  R$_3$ and R$_9$ are, independently, —H or C$_{1-2}$ alkyl;
  R$_2$ and R$_8$ are, independently, —H or C$_{1-2}$ alkyl
further provided that:
  (a) when R$_2$ and R$_8$ are, independently, —H or C$_{1-2}$ alkyl and R$_1$ or R$_0$ is 4-pyridyl, then the other of R$_1$ and R$_0$ is other than mono-C$_{1-2}$ alkoxy-substituted phenyl or mono-halo-substituted phenyl.

In addition to the methods of the present invention, and the compounds of Formula (IA) this invention also relates to the interemediate compounds shown below.

This invention relates to a compound of the formula:

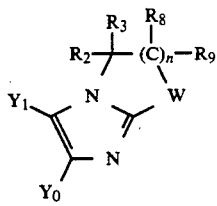

FORMULA (D)

, or a pharmaceutically acceptable salt thereof, wherein:
W is —CR$_5$=CR$_7$—, —N=CR$_7$—, —S— or —O—;
Y$_1$ is 4-(1,4-dihydro)pyridyl substituted with N-(C$_{1-8}$ alkanoyl), N-(C$_{1-8}$ alkoxycarbonyl), N-benzoyl, N-phenoxycarbonyl, N-phenylacetyl, or N-benzyloxycarbonyl;
Y$_0$ is (a) monosubstituted phenyl wherein said substituent is C$_{1-3}$ alkylthio, C$_{1-2}$ alkoxy, halo, —H, or C$_{1-4}$ alkyl; or (b) disubstituted phenyl wherein said substituent are, independently, C$_{1-3}$ alkylthio, C$_{1-2}$ alkoxy, halo, C$_{1-4}$ alkyl, or the disubstituents together form a methylene dioxy group;
provided that:
(1.) when W is —CR$_5$=CR$_7$— or —N=CR$_7$— then
n is 1;
R$_3$, R$_5$, R$_7$ and R$_9$ are, independently, —H or C$_{1-2}$ alkyl;
R$_2$ and R$_8$ together represent a double bond across the two adjacent carbon atoms in the B ring so as to form an aromatic pyridine or pyrimidine ring; and
(2.) when W is —S— or —O— then
n is 1;
R$_3$ and R$_9$ are, independently, —H or C$_{1-2}$alkyl; and
R$_2$ and R$_8$ together represent a double bond in the B ring such that the B ring is an aromatic thiazole or oxazole ring.

This invention also relates to a compound of the formula:

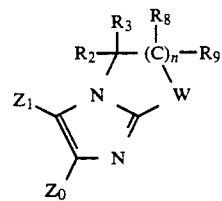

FORMULA (E)

, or a pharmaceutically acceptable salt thereof, wherein:
W is —CR$_5$=CR$_7$—, —N=CR$_7$—, —S— or —O—;
one of Z$_1$ and Z$_0$ is 4-(1,2-dihydro-2-alkyl)pyridyl substituted with N-(C1-8 alkanoyl), N-(C1-8 alkoxycarbonyl), N-benzoyl, N-phenoxycarbonyl, N-phenylacetyl, or N-benzyloxycarbonyl; and the other of Z$_1$ and Z$_0$ is
(a) monosubstituted phenyl wherein said substituent is selected from C$_{1-3}$ alkylthio, C$_{1-2}$ alkoxy, halo, —H, or C$_{1-4}$ alkyl; or
(b) disubstituted phenyl wherein said substituents are independently selected from C$_{1-3}$ alkylthio, C$_{1-2}$ alkoxy, halo, C$_{1-4}$ alkyl, or the disubstituents together form a methylene dioxy group;

provided that:
(1.) when W is —CR$_5$=CR$_7$— or —N=CR$_7$— then
n is 1;
R$_3$, R$_5$, R$_7$ and R$_9$ are, independently, —H or C$_{1-2}$ alkyl;
R$_2$ and R$_8$ together represent a double bond in the B ring such that the B ring is an aromatic pyridine or pyridine ring; and
(2.) when W is —S— or —O— then
n is 1;
R$_3$ and R$_9$ are, independently, —H or C$_{1-2}$alkyl; and
R$_2$ and R$_8$ are, independently, —H or C$_{1-2}$ alkyl or together represent a double bond in the B ring such that the B ring is an aromatic thiazole or oxazole ring.

This invention also relates to a compound of the formula:

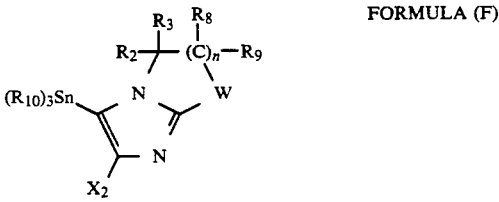

FORMULA (F)

wherein:
W is —CR$_5$=CR$_7$—, —N=CR$_7$—, —S— or —O—;
R$_{10}$ is C$_{1-4}$ alkyl; and
X$_2$ is 4-pyridyl or mono-C$_{1-4}$alkyl-substituted pyridyl;
provided that:
(1.) when W is —CR$_5$=CR$_7$— or —N=CR$_7$— then
n is 1;
R$_3$, R$_5$, R$_7$ and R$_9$ are, independently, —H or C$_{1-2}$ alkyl;
R$_2$ and R$_8$ together represent a double bond in the B ring such that the B ring is an aromatic pyridine or pyrimidine ring; and
(2.) when W is —S— then
n is 1 or 2;
R$_3$ and R$_9$ are, independently, —H or C$_{1-2}$ alkyl;
further provided that:
(a) when W is —S— and n is 1 then R$_2$ and R$_8$ are, independently, —H or C$_{1-2}$ alkyl or together represent a double bond in the B ring such that the B ring is an aromatic thiazole ring; and
(b) when W is —S— and n is 2 then R$_2$ and R$_8$ are, independently, —H or C$_{1-2}$ alkyl; and
(3.) when W is —O— then
n is 1;
R$_3$ and R$_9$ are, independently, —H or C$_{1-2}$ alkyl; and
R$_2$ and R$_8$ repesent double bonds in the B ring such that the B ring is an aromatic oxazole ring.

This invention also relates to a compound of the formula:

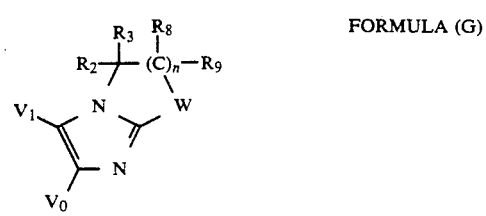

FORMULA (G)

, or a pharmaceutically acceptable salt thereof,
wherein
W is $-CR_5=CR_7-$, $-N=CR_7-$, $-S-$ or $-O-$;
one of $V_1$ or $V_0$ is 4-pyridyl or $C_{1-4}$alkyl-4-pyridyl, provided that when $V_1$ is $C_{1-4}$alkyl-4-pyridyl the alkyl substitutent is located at the 2-position of the pyridine ring, and the other of $V_1$ and $V_0$ is selected from:
   (a) monosubstituted phenyl wherein said substituent is mercapto; or
   (b) disubstituted phenyl wherein one of said substituents must be mercapto and the other is selected from mercapto, $C_{1-2}$ alkoxy, halo, or $C_{1-4}$ alkyl;
provided that:
   (1.) when W is $-CR_5=CR_7-$ or $-N=CR_7-$ then
      n is 1;
      $R_3$, $R_5$, $R_7$ and $R_9$ are, independently, $-H$ or $C_{1-2}$ alkyl; and
      $R_2$ and $R_8$ together represent a double bond in the B ring such that the B ring is an aromatic pyridine or pyrimidine ring; and
   (2.) when W is $-S-$ then
      n is 1 or 2;
      $R_3$ and $R_9$ are, independently, $-H$ or $C_{1-2}$ alkyl; further provided that:
         (a) when W is $-S-$ and n is 1 then $R_2$ and $R_8$ are, independently, $-H$ or $C_{1-2}$ alkyl or together represent a double bond in the B ring such that the B ring is an aromatic thiazole ring; and
         (b) when W is $-S-$ and n is 2 then $R_2$ and $R_8$ are, independently, $-H$ or $C_{1-2}$ alkyl; and
   (3.) when W is $-O-$ then
      n is 1;
      $R_3$ and $R_9$ are, independently, $-H$ or $C_{1-2}$ alkyl; and
      $R_2$ and $R_8$ repesent double bonds in the B ring such that the B ring is an aromatic oxazole ring.

This invention also relates to a compound of the formula:

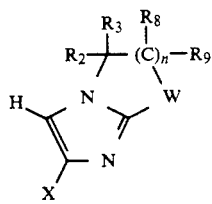

FORMULA (C)

, or a pharmaceutically acceptable salt thereof,
wherein:
W is $-CR_5=CR_7-$, $-N=CR_7-$, $-S-$ or $-O-$;
X is
   a) 4-pyridyl or mono-$C_{1-4}$ alkyl-substituted pyridyl;
   b) b) phenyl or monosubstituted phenyl wherein the substituent is selected from hydrogen, halo, $C_{1-4}$ alkyl, $C_{1-3}$ alkylthio, or $C_{1-2}$ alkoxy; or
   c) disubstituted phenyl wherein the substituents are selected from halo, $C_{1-3}$ alkylthio, $C_{1-3}$ alkyl, $C_{1-2}$ alkoxy, or the disubstituents together form a methylene dioxy group;
provided that:
   (1.) when W is $-CR_5=CR_7-$ or $-N=CR_7-$ then
      n is 1;
      $R_3$, $R_5$, $R_7$ and $R_9$ are, independently, $-H$ or $C_{1-2}$ alkyl;
      $R_2$ and $R_8$ together represent a double bond in the B ring such that the B ring is an aromatic pyridine or pyrimidine ring; and
   (2.) when W is $-S-$ then
      n is 1 or 2;
      $R_3$ and $R_9$ are, independently, $-H$ or $C_{1-2}$ alkyl; further provided that:
         (a) when W is $-S-$ and n is 1 then $R_2$ and $R_8$ are, independently, $-H$ or $C_{1-2}$ alkyl or together represent a double bond in the B ring such that the B ring is an aromatic thiazole ring; and
         (b) when W is $-S-$ and n is 2 then $R_2$ and $R_8$ are, independently, $-H$ or $C_{1-2}$ alkyl; and
   (3.) when W is $-O-$ then
      n is 1;
      $R_3$ and $R_9$ are, independently, $-H$ or $C_{1-2}$ alkyl;
      $R_2$ and $R_8$ together represent a double bond in the B ring such that the B ring is an aromatic oxazole ring.

By the term "halo" as used herein is meant all halogens, i.e., chloro, fluoro, bromo and iodo.

By the term "inhibiting the production of IL-1" is meant the down regulation of excessive in vivo IL-1 levels in a human to normal levels.

By the term "production of IL-1 by monocytes and/or macrophages" is meant the in vivo release of IL-1 by such cells.

By the term "inhibiting the production of TNF" is meant the down regulation of excessive in vivo TNF levels in a human to normal levels.

By the term "production of TNF by monocytes and/or macrophages" is meant the in vivo release of TNF by such cells.

The discovery of a compound which specifically inhibits TNF production will not only contribute to the understanding of how this molecule is synthesized, processed and secreted, but will also provide a therapeutic approach for diseases in which excessive or unregulated TNF production is implicated. As TNF-$\beta$(also known as lymphotoxin) has close structural homology with TNF-a (also known as cachectin) and since each induces similiar biologic responses and binds to the same cellular receptor, both TNF-a and TNF-$\beta$ are both inhibited by the compounds of the present invention and thus are herein referred to collectively as "TNF" unless specifically delineated otherwise.

By the term "sulfinyl" as used herein is meant the oxide of the corresponding sulfide. By the term "thio" as used herein is meant the sulfide. For further clarification, the following table outlines the structural attachment of the atoms of the $R_1$ and $R_0$ substituents of the compounds of Formula (I) and Formula (II):

| $R_1$ or $R_0$ | Structural Attachment |
|---|---|
| $C_{1-3}$ alkylsulfinyl | [AS(O)-] |
| $C_{2-5}$ 1-alkenyl-1-thio | [AA$^1$C=CHS-] |
| $C_{2-5}$ 1-alkenyl-1-sulfinyl | [AA$^1$C=CHS(O)-] |
| $C_{3-5}$ 2-alkenyl-1-thio | [ACH=CA$^1$CH$_2$S-] |
| $C_{3-5}$ 2-alkenyl-1-sulfinyl | [ACH=CA$^1$CH$_2$S(O)-] |
| 1-acyloxy-1-alkythio | [AC(O)OCH(A$^1$)S-] |

NOTE:
A and $A^1$ are hydrogen or alkyl;

The preparation of all compounds of Formula (I) and (II) and pharmaceutically acceptable salts thereof wherein $W_1$ is $-(CR_4R_5)-(CR_6R_7)-$; n is 0 or 1; $R_2$, $R_3$, $R_4$, $R_5$, $R_6$, $R_7$, $R_8$ and $R_9$ are H or one or more of $R_2$, $R_3$, $R_4$, $R_5$, $R_6$, $R_7$, $R_8$ and $R_9$ are independently selected from H or $C_{1-2}$ alkyl; and one of $R_0$ or $R_1$ is 4-pyridyl or mono-$C_{1-4}$alkyl-substituted-4-pyridyl, is disclosed in Bender et al., U.S. patent application Ser. No. 07/255,816, filed Oct. 11, 1988, the disclosure of which is hereby incorporated by reference.

The preparation of all compounds of Formula (I) and (II) and pharmaceutically acceptable salts thereof wherein $W_1$ is $S(O)_m$; m is 0, 1 or 2; n is 1 or 2; $R_2$, $R_3$, $R_4$, $R_5$, $R_6$, $R_7$, $R_8$ and $R_9$ are H or one or more of $R_2$, $R_3$, $R_4$, $R_5$, $R_6$, $R_7$, $R_8$ and $R_9$ are independently selected from H or $C_{1-2}$ alkyl; and $R_1$ or $R_0$ is 4-pyridyl, other than those compounds wherein $R_1$ or $R_0$ is monosubstituted phenyl wherein said substituent is selected from $C_{2-5}$ 1-alkenyl-1-thio, $C_{2-5}$ 1-alkenyl-1-sulfinyl, $C_{2-5}$ 2-alkenyl-1-thio or $C_{2-5}$ 2-alkenyl-1-sulfinyl, 1-acyloxy-1-alkylthio or disubstituted phenyl wherein said substitutents are selected from one of the following combinations: di($C_{1-3}$ alkylthio), dihalo, $C_{1-3}$ alkylthio and $C_{1-2}$ alkoxy, $C_{1-3}$ alkylthio and halo, $C_{1-3}$ alkylthio and $C_{1-4}$ alkyl, or $C_{1-2}$ alkoxy and halo, or disubstituted phenyl wherein the substituents are the same and are selected from; $C_{1-3}$ alkylsulfinyl, $C_{2-5}$ 1-alkenyl-1-thio, $C_{2-5}$ 1-alkenyl-1-sulfinyl, $C_{3-5}$ 2-alkenyl-1-thio, $C_{3-5}$ 2-alkenyl-1-sulfinyl or 1-acyloxy-1-alkylthio, or disubstituted phenyl wherein one of said substituents must be $C_{1-3}$ alkylthio, $C_{1-3}$ alkylsulfinyl, $C_{2-5}$ 1-alkenyl-1-thio, $C_{2-5}$ 1-alkenyl-1sulfinyl, $C_{3-5}$ 2-alkenyl-1-thio, $C_{3-5}$ 2-alkenyl-1-sulfinyl or 1-acyloxy-1-alkylthio and the other is selected from $C_{1-2}$ alkoxy, halo, or $C_{1-4}$ alkyl is disclosed in Bender et al., U.S. Pat. No. 4,175,127, issued Nov. 20, 1979, Bender et al., U.S. patent application Ser. No. 07/106,199 filed on Jul. 10, 1987 or Bender et al., U.S. Pat. No. 4,803,279, issued Feb. 9, 1989, the entire disclosures of all of which are hereby incorporated by reference.

The preparation of the compounds of Formula (II) and pharmaceutically acceptable salts thereof wherein $W_1$ is —($CR_4R_5$)—($CR_6R_7$)—; n is 0, $R_4$ and $R_5$ together are oxo; or when one of $R_4$ and $R_5$ is H the other of $R_4$ and $R_5$ is OH; or when $R_4$ and $R_5$ are both fluoro substituents are disclosed in Gallagher et al., *Tetrahedron Letters*, Vol. 30, No. 48, pp.6599–6602 (1989) the entire disclosure of which is hereby incorporated by reference.

The preparation of all the remaining compounds of Formula (I) not already described above, including all the compounds of Formula (IA), can be carried out by one of skill in the art according to the procedures outlined in the Examples, infra.

All of the compounds of Formula (I) and (II) are usfule in the methods of the subject invention, i.e. methods of inhibiting the production of IL-1 or TNF by macrophages and/or monocytes in a human in need thereof.

All the compounds of Formula (C), Formula (D), Formula (E), Formula (F) and Formula (G) are useful as intermediates in the preparation of the compounds of Formula (IA). The preparation of all the compounds of Formula (C), Formula (D), Formula (E), Formula (F) and Formula (G) can be carried out by one of skill in the art according to the procedures outlined in the Examples, infra.

Pharmaceutically acceptable salts and their preparation are well known to those skilled in pharmaceuticals. Pharmaceutically acceptable salts of the compounds of Formula (I) or Formula (II) which are useful in the present invention include, but are not limited to, maleate, fumarate, lactate, oxalate, methanesulfonate, ethane-sulfonate, benzenesulfonate, tartrate, citrate, hydrochloride, hydrobromide, sulfate and phosphate salts. Preferred pharmaceutically acceptable salts of the compounds of Formula (I) or Formula (II) include hydrochloride and hydrobromide salts, and such salts can be prepared by known techniques such as the method of Bender et al., U.S. Pat. No. 4,175,127, the disclosure of which is hereby incorporated by reference.

Preferred compounds of Formula (IA) include those wherein:

W is —$CR_5$=$CR_7$—, —N=$CR_7$—, —$S(O)_m$— or —O—;

one of $R_1$ and $R_0$ is 4-pyridyl or $C_{1-2}$ alkyl-4-pyridyl, provided that when $R_1$ is $C_{1-2}$ alkyl-4-pyridyl the alkyl substituent is located at the 2-position of the pyridine ring, and the other of $R_1$ and $R_0$ is
  (a) monosubstituted phenyl wherein said substituent is $C_{1-2}$ alkylthio, $C_{1-2}$ alkylsulfinyl, $C_{2-3}$ 1-alkenyl-1-thio, 2-propenyl-1-thio, 1-acyloxy-1-alkylthio, $C_{1-2}$ alkoxy, halo; or
  (b) disubstituted phenyl wherein said substitutents are, independently, $C_{1-2}$alkylthio or $C_{1-2}$ alkoxy; or
  (c) disubstituted phenyl wherein one of said substituents is $C_{1-2}$ alkylsulfinyl, $C_{2-3}$ 1-alkenyl-1-thio, 2-propenyl-1-thio or 1-acyloxy-1-alkylthio and the other is $C_{1-2}$ alkoxy; or
  (d) disubstituted phenyl wherein the substituents are the same and are $C_{1-2}$ alkylsulfinyl, $C_{2-3}$ 1-alkenyl-1-thio, 2-propenyl-1-thio or 1-acyloxy-1-alkylthio or wherein the substituents together form a methylene dioxy group;

provided that:
(1.) when W is —$CR_5$=$CR_7$— or —N=$CR_7$— then
  n is 1;
  $R_3$, $R_5$, $R_7$ and $R_9$ are —H;
  $R_2$ and $R_8$ together represent a double bond in the B ring such that the B ring is an aromatic pyridine or pyrimidine ring; and
(2.) when W is $S(O)_m$;
  m is 0, 1 or 2;
  n is 1 or 2;
  $R_3$ and $R_9$ are —H; and
  $R_2$ and $R_8$ are —H; then one of $R_1$ or $R_0$ is 4-pyridyl, and the other of $R_1$ and $R_0$ is:
  (a) monosubstituted phenyl wherein said substituent is selected from $C_{2-3}$ 1-alkenyl-1-thio, 2-propenyl-1-thio or 1-acyloxy-1-alkylthio; or
  (b) disubstituted phenyl wherein said substituents are $C_{1-2}$ alkylthio; or
  (c) disubstituted phenyl wherein one of said substituents must be $C_{1-2}$ alkylthio, $C_{1-2}$ alkylsulfinyl, $C_{2-3}$ 1-alkenyl-1-thio, 2-propenyl-1-thio or 1-acyloxy-1-alkylthio and the other is $C_{1-2}$ alkoxy; and
(3.) when W is $S(O)_m$;
  m is 0;
  n is 1; and
  $R_2$ and $R_8$ together represent a double bond in the B ring such that the B ring is an aromatic thiazole ring; then
  $R_3$ and $R_9$ are, —H; and
(4.) when W is —O— then
  n is 1;
  $R_3$ and $R_9$ are —H; and $R_2$ and $R_8$ together represent a double bond in the B ring such that the B ring is an aromatic oxazole ring.

The most preferred compound of Formula (IA) is 2-(4-methoxyphenyl)-3(4-pyridyl)-imidazo[1,2-a]-pyridine.

Preferred compounds of Formula (1) include those wherein:

$W_1$ is —$(CR_4R_5)$—$(CR_6R_7)$—, —$CR_5$=$CR_7$—, or —$S(O)_m$—;

one of $R_1$ and $R_0$ is 4-pyridyl or $C_{1-2}$ alkyl-4-pyridyl, provided that when $R_1$ is $C_{1-2}$ alkyl-4-pyridyl the alkyl substituent is located at the 2-position of the pyridine ring, and the other of $R_1$ and $R_0$ is:
(a) monosubstituted phenyl wherein said substituent is $C_{1-2}$ alkylthio, $C_{1-2}$ alkylsulfinyl, 1-acyloxy-1-alkylthio, $C_{1-2}$ alkoxy or halo, or
(b) disubstituted phenyl wherein said subsdtutents are, independently, $C_{1-2}$ alkylthio or $C_{1-2}$ alkoxy, or
(c) disubstituted phenyl wherein one of said substituents is $C_{1-2}$ alkylsulfinyl or 1-acyloxy-1-alkylthio and the other is $C_{1-2}$ alkoxy, or
(d) disubstituted phenyl wherein the substituents are the same and are $C_{1-2}$ alkylsulfinyl or 1-acyloxy-1-alkylthio or wherein the substituents together form a methylene dioxy group;

provided that:
(1.) when $W_1$ is —$(CR_4R_5)$—$(CR_6R_7)$— then
n is 0 or 1; and
$R_2$, $R_3$, $R_4$, $R_5$, $R_6$, $R_7$, $R_8$, and $R_9$ are —H; and
when $R_1$ or $R_0$ is 4-pyridyl, the other of $R_1$ and $R_0$ is other than mono-$C_{1-2}$ alkoxy-substituted phenyl or mono-halo-substituted phenyl;
when n is 0, $R_4$ and $R_5$ together are oxo; $R_4$ and $R_5$ may both be fluoro, or one of $R_4$ and $R_5$ is H and the other is OH;

(2.) when $W_1$ is —$CR_5$=$CR_7$—, then
n is 1;
$R_3$, $R_5$, $R_7$ and $R_9$ are —H; and
$R_2$ and $R_8$ together represent a double bond in the B ring such that the B ring is an aromatic pyridine ring;

(3.) when $W_1$ is $S(O)_m$ then
m is 0, 1 or 2;
n is 1 or 2; and
$R_3$ and $R_9$ are —H;
$R_2$ and $R_8$ are —H or $R_2$ and $R_8$ together represent a double bond in the B ring such that the B ring is an aromatic thiazole ring;
further provided that:
(a) when $R_2$ and $R_8$ are —H and $R_1$ or $R_0$ is 4-pyridyl, then the other of $R_1$ and $R_0$ is other than mono-$C_{1-2}$ alkoxy-substituted phenyl or mono-halo-substituted phenyl; and
(b) when $R_2$ and $R_8$ together represent a double bond in the B ring such that the B ring is an aromatic thiazole ring, then m is 0 and n is 1; and (4) when $W_1$ is —O— then
n is 1;
$R_3$ and $R_9$ are —H; and
$R_2$ and $R_8$ together represent a double bond in the B ring such that the B ring is an aromatic oxazole ring.

Especially preferred compounds of Formula (I) having superior IL-1 inhibiting activity include the following:

2-(4-methylthiophenyl)-3-(4-pyridyl)-6,7-dihydro-[5H]-pyrrolo[1,2-a]imidazole;
2-(4-methylsulfinylphenyl)-3-(4-pyridyl)-6,7-dihydro-[5H]-pyrrolo[1,2-a]imidazole;
2-(4-ethylthiophenyl)-3-(4-pyridyl)-6,7-dihydro-[5H]-pyrrolo[1,2-a]imidazole;
2-(4-ethylsulfinylphenyl)-3-(4-pyridyl)-6,7-dihydro-[5H]-pyrrolo[1,2-a]imidazole;
2-(4-methylthiophenyl)-3-(4-(2-methyl)pyridyl)-6,7-dihydro-[5H]-pyrrolo[1,2-a]imidazole;
2-(4-methylsulfinyiphenyl)-3-(4-(2-methyl)pyridyl)-6,7-dihydro-[5H]-pyrrolo[1,2-a]imidazole;
2-(4-methoxyphenyl)-3-(4-pyridyl)-imidazo[1,2-a]-pyridine;
5-(3,4-(methylenedioxy)phenyl)-6-(4-pyridyl)-2,3-dihydroimidazo 2,1-b]thiazole;
2-(4-methoxyphenyl)-3-(4-(2-methyl)pyridyl)-6,7-dihydro-[5H]-pyrrolo-[1,2-a]imidazole;
2-(4-acetoxymethylthiophenyl)-3-(4-(2-methyl)-pyridyl)-6,7-dihydro[5H]-pyrrolo[1,2-a]imidazole.
2-(trimethylacetylthiophenyl)-3-(4-pyridyl)-6,7 -dihydro- [5H]-pyrrolo[1,2-a]imidazole;
6-(4-methylthiophenyl)-5-(4-pyridyl)-2,3-dihydro-imidazo[2,1-b]-thiazole;
5-(4-methylthiophenyl)-6-(4-pyridyl)-2,3-dihydro-imidazo[2,1-b]-hiazole;
3-(4-methylthiophenyl)-2-(4-pyridyl)-6,7-dihydro-[5H]-pyrrolo[1,2-a]imidazole;
2-(4-propylthiophenyl)-3-(4-pyridyl)-6,7-dihydro-[5H]-pyrrolo[1,2-al-imidazole;
2-(4-methylthiophenyl)-3-(4-(2-ethyl)pyridyl)-6,7-dihydro-[5H]-pyrrolo-[1,2-a]-imidazole;
2-(4-Mercaptophenyl)-3-(4-pyridyl)-6,7-dihydro-[5H]-pyrrolo[1,2-a]-imidazole disulfide;
2-(4-Methoxyphenyl)-3-(4-pyridyl)-7-oxo-5,6-dihydro-[7H]-pyrrolo[1,2-a]-imidazole;
5,6-dihydro-2-(4-Methoxyphenyl)-3-(4-pyridyl)-[7H]-pyrrolo-[1,2-a]-imidazole-7-ol; and
5,6-dihydro-7,7-difluoro-2-(4-Methoxyphenyl)-3-(4-pyridyl)-[7H]-pyrrolo-[1,2-a]-imidazole.

Preferred compounds useful in the method of inhibition of the production of TNF of the subject invention include those compounds of Formula (II) wherein:

$W_1$ is —$(CR_4R_5)$—$(CR_6R_7)$—, —$CR_5$=$CR_7$—, or —$S(O)_m$—;

one of $R_1$ and $R_0$ is 4-pyridyl or $C_{1-2}$ alkyl-4-pyridyl, provided that when $R_1$ is $C_{1-2}$ alkyl-4-pyridyl the alkyl substituent is located at the 2-position of the pyridine ring, and the other of $R_1$ and $R_0$ is
(a) monosubstituted phenyl wherein said substituent is $C_{1-2}$ alkylthio, $C_{1-2}$ alkylsulfinyl, 1-acyloxy-1-alkylthio, $C_{1-2}$ alkoxy or halo, or
(b) disubstituted phenyl wherein said substitutents are, independently, $C_{1-2}$ alkylthio or $C_{1-2}$ alkoxy, or
(c) disubstituted phenyl wherein one of said substituents is $C_{1-2}$ alkylsulfinyl or 1 -acyloxy-1 -alkylthio and the other is $C_{1-2}$ alkoxy, or
(d) disubstituted phenyl wherein the substituents are the same and are $C_{1-2}$ alkylsulfinyl or 1-acyloxy-1 -alkylthio or wherein the substituents together form a methylene dioxy group;

provided that:
(1.) when $W_1$ is —$(CR_4R_5)$—$(CR_6R_7)$— then
n is 0;
and $R_4$ and $R_5$ may together form an oxo; $R_4$ and $R_5$ are both fluoro; or one of $R_4$ and $R_5$ is H and the other OH; or (2.) when $W_1$ is $-CR_5=CR_7-$ or $-N=CR_7-$ then
n is 1;
$R_3$, $R_5$, $R_7$ and $R_9$ are, independently, —H or $C_{1-2}$ alkyl; and
$R_2$ and $R_8$ together represent a double bond in the B ring such that the B ring is an aromatic pyridine or pyrimidine ring;
(3.) when $W_1$ is $S(O)_m$ then
m is 0, 1 or 2;
n is 1 or 2; and
$R_3$ and $R_9$ are, independently, —H or $C_{1-2}$ alkyl;
$R_2$ and $R_8$ are, independently, —H or $C_{1-2}$ alkyl or $R_2$ and $R_8$ together represent a double bond in the B ring such that the B ring is an aromatic thiazole ring;
further provided that:
(a) when $R_2$ and $R_8$ are, independently, —H or $C_{1-2}$ alkyl and $R_1$ or $R_0$ is 4-pyridyl, then the other of $R_1$ and $R_0$ mono-fluoro-substituted phenyl; and
(b) when $R_2$ and $R_8$ together represent a double bond in the B ring such that the B ring is an aromatic thiazole ring, then m is 0 and n is 1; and
(4.) when $W_1$ is —O— then
n is 1; $R_3$ and $R_9$ are, independently, —H or $C_{1-2}$ alkyl; and
$R_2$ and $R_8$ together represent a double bond in the B ring such that the B ring is an aromatic oxazole ring;
or a pharmaceutically acceptable salt thereof.

Additional preferred compounds of Formula (II) are when
(1.) when $W_1$ is $-(CR_4R_5)-(CR_6R_7)-$;
n is 0; and $R_2$ and $R_8$ are, independently, —H or $C_{1-2}$ alkyl and $R_1$ or $R_0$ is 4-pyridyl or C1-4alkyl-4-pyridyl, then the other of $R_1$ and $R_0$ is a mono-$C_{1-3}$alkylthio, $C_{1-3}$ alkylsulfinylphenyl or a mono-halo-substituted phenyl;
(2) when $W_1$ is $S(O)_m$;
m is 0, 1 or 2; n is 1 or 2; and $R_2$ and $R_8$ are, independently, —H or $C_{1-2}$ alkyl and $R_1$ or $R_0$ is 4-pyridyl, then the other of $R_1$ and $R_0$ is other than mono-fluoro-substituted phenyl.

Especially preferred compounds for use in the method of the subject invention for inhibition of TNF production are
2-Phenyl-3-pyridyl-6,7-dihydro-[5H]-pyrrolo-[1,2-a]-imidazole;
2-4-Bromophenyl-3-pyridyl-6,7-dihydro- [5H]-pyrrolo-[1,2-a]-imidazole;
2-(4-Methylthiophenyl)-3-(4-pyridyl)-6,7-dihydro-[5H]-pyrrolo-[1,2-a]-imidazole;
2-(4-Fluorophenyl)- 3- (4-pyridyl)-6,7 -dihydro-[5H]-pyrrolo- [1,2-a]-imidazole;
3-(4-Fluorophenyl)-2- (4- pyridyl) -6,7-dihydro- [5H]-pyrrolo- [1,2-a]-imidazole;
2-(4-Pyridyl)-3-(4-methyl thiophenyl) -6,7-dihydro-[5H]-pyrrolo-[1,2-a]-imidazole;
2-(4-Methylthiophenyl)-3-[4-(2-methylpyridyl)]-6,7-dihydro-[5H]-pyrrolo[1,2-a]-imidazole;
2-(4-Methoxyphenyl)-3-(4-pyridyl)-7-oxo-5,6-dihydro-7H-pyrrolo[1,2-a]imidazole;
5,6-Dihydro-2-(4-methoxyphenyl)-3-(4-pyridyl)-[7H]-pyrrolo-[1,2-a]-imidazole-7-ol;
2-(4-Acetoxymethylthiophenyl)-3-(4-pyridyl)-6,7-dihydro-[5H]-pyrrolo[1,2-a]-imidazole;
2-(4-Methoxyphenyl)-3-(4-pyridyl)-6,7-dihydro-[5H]-pyrrolo[1,2-a]imidazole;
2-(4-Methylsulfoxyphenyl)-3-(4-pyridyl)-6,7-dihydro[5H]-pyrrolo[1,2]-imidazole;
2-(4-Ethylthiophenyl)-3-(4-pyridyl)-6,7-dihydro-[5H]-pyrrolo-[1,2-a]-imidazole; or
2-(4-Ethylsulfonylphenyl)-3-(4-pyridyl)-6,7-dihydro-[5H]-pyrrolo-[1,2-a]-imidazole.

Also found to possess inhibition of TNF production are the following compounds, which are useful in the process of using this invention:
6-(4-Fluorophenyl)-5-(4'-pyridyl)-2,3-dihydroimidazo-[2, I-b]thiazole-1-oxide;
6-(4-Fluorophenyl)-5-(4-pyridyl)-2,3-dihydroimidazo[2,1-b]thiazole-1,1-dioxide; or
5-(4-Fluorophenyl)-6-(4'-pyridyl)-2,3-dihydroimidazo[2,1-b]thiazole.

Interleukin-1 (IL-1) has been demonstrated to mediate a variety of biological activities thought to be important in immunoregulation and other physiological conditions such as inflammation [See, e.g., Dinarello et al., *Rev. Infect. Disease*, 6, 51 (1984)]. The myriad of known biological activities of IL-1 include the activation of T helper cells, induction of fever, stimulation of prostaglandin or collagenase production, neutrophil chemotaxis, induction of acute phase proteins and the suppression of plasma iron levels.

The discovery of a compound which specifically inhibits IL-1 production will not only contribute to the understanding of how this molecule is synthesized, processed and secreted, but will also provide a therapeutic approach for diseases in which excessive or unregulated IL-1 production is implicated.

It has now been discovered that compounds of Formula (I) and Formula (II) and their pharmaceutically acceptable salts thereof, are useful for inhibiting the production of IL-1 and TNF by monocytes and/or macrophages in a human in need of such inhibition. It should be noted that the compounds of Formula (I) and Formula (II) wherein $R_1$ or $R_0$ is a phenyl substituted by a $C_{1-3}$ alkylsulfinyl, $C_{2-5}$ 1-alkenyl-1-sulfinyl, or $C_{2-5}$ 2-alkenyl-1-sulfinyl group are predrugs which are reductively converted in vivo to the corresponding alkylthio or alkenylthio form.

There are several disease states in which excessive or unregulated IL-1 production by monocytes and/or macrophages is implicated in exacerbating and/or causing the disease. These include rheumatoid arthritis [See, e.g., Fontana et al., *Arthritis Rheum.*, 22, 49–53 (1982)]; osteoarthritis [See, e.g., Wood et al., *Arthritis Rheum.*, 26, 975 (1983)]; endotoxemia and/or toxic shock syndrome [See, e.g., Ikejima and Dinarello, *J. Leukocyte Biology*, 37, 714 (1985)]; other acute or chronic inflammatory disease states such as the inflammatory reaction induced by endotoxin [See, e.g., Habicht and Beck, *J. Leukocyte Biology*, 37, 709 (1985)]; and inflammatory bowel disease [See, e.g., Satsangi et al., *Clin. Exp. Immunol.*, 67, 594–605 (1987)]; other chronic inflammatory disease states such as tuberculosis. [See, e.g., Chesque et al., *J. Leukocyte Biology*, 37, 690 (1985)]; atherosclerosis [See, e.g., Albrightson et al., *J. Immunol.*, 135, 1872–1877 (1985)]; muscle degeneration See, e.g., Baracos et al., *N. Eng. J. Med.*, 308, 553–558 (1983)]; and cachexia [See, e.g., Beutler et al., *J. Immunol.*, 135, 3969–3971 (1985)]. Benjamin et al., "Annual Reports in Medicinal Chemistry—20", Chapter 18, pages 171–183 (1985), Academic Press, Inc., disclose that excessive IL-1 production is implicated in: Psoriatic arthritis, Reitem's syndrome, Rheumatoid arthritis, Osteoarthritis, Gout, Traumatic arthritis, Rubella arthritis, and Acute synovitis.

Dinarello, *J. Clinical Immunology,* 5 (5), 287-297 (1985), reviews the biological activities which have been attributed to IL-1 and such activities are summarized in Table A. It should be noted that some of these effects have been described by others as indirect effects of IL-1.

TABLE A

| Biological Activities Attributed to IL-1 |
| --- |
| Fever (in rabbits, mice and rats) |
| Hypoferremia |
| Hypozincemia |
| Hypercupremia |
| Increased |
| Blood neutrophils |
| Hepatic acute-phase proteins |
| Bone resorption |
| Cartilage breakdown |
| Muscle proteolysis |
| Slow-wave sleep |
| Endothelial procoagulant |
| Chondrocyte proteases |
| Synovial collagenase |
| Endothelial neutrophil adherence |
| Neutrophil degranulation |
| Neutrophil superoxide |
| Interferon production |
| Profileration of |
| Fibroblasts |
| Glial cells |
| Mesangial cells |
| Synovial fibroblasts |
| EBV B-cell lines |
| Chemotaxis of |
| Monocytes |
| Neutrophils |
| Lymphocytes |
| Stimulation of $PGE_2$ in |
| Hypothalamus |
| Cortex |
| Skeletal muscle |
| Dermal fibroblast |
| Chondrocyte |
| Macrophage/monocyte |
| Endothelium ($PGI_2$) |
| Decreased |
| Hepatic albumin synthesis |
| Appetite |
| Brain binding of opiods |
| Augmentation of |
| T-cell responses |
| B-cell responses |
| NK activity |
| IL-2 production |
| Lymphokine production |

An effective, IL-1 production inhibiting amount of a compound of Formula (I) or a pharmaceutically acceptable salt thereof is useful in treating, prophylactically or therapeutically, any disease state in a human which is exacerbated or caused by excessive or unregulated IL-1 production by such human's monocytes and/or macrophages.

This invention relates to the use of a compound of Formula (I), or a pharmaceutically acceptable salt thereof in the manufacture of a medicament for the treatment of prophylactically or therapeutically, any disease state in a human which is exacerbated or caused by excessive or unregulated IL-1 or production by such human's monocytes and/or macrophages.

The discovery of a compound which specifically inhibits TNF production will not only contribute to the understanding of how this molecule is synthesized, processed and secreted, but will also provide a therapeutic approach for diseases in which excessive or unregulated TNF production is implicated.

There are several disease states in which excessive or unregulated TNF production by monocytes and/or macrophages is implicated in exacerbating and/or causing the disease. These include endotoxemia and/or toxic shock syndrome [See Tracey et al., *Nature* 330:662-664 (1987); Badger et al., *Circ. Shock,* 27:51-61 (1989) and Hinshaw et al., *Circ. Shock* 30:279-292 (1990)]; cachexia [See, Dezube et al., *Lancet,* 335 (8690):662 (1990)]; Adult Respiratory Distress Syndrome where TNF concentration in excess of 12,000 pg/ml have been detected in pulmonay aspirates from ARDS patients. [See, Millar et al., *Lancet* 2(8665):712-714 (1989). Systemic infusion of recombinant TNF resulted in changes typically seen in ARDS [See, Ferrai-Baliviera et al., *Arch. Surg.* 124(12):1400-1405 (1989)]; AIDS viral replication of latent HIV in T-cell and macrophage lines can be induced by TNF [See, Folks et al., *PNAS* 86:2365-2368 (1989)]. A molecular mechanism for the virus inducing activity is suggested by TNFs ability to activate a gene regulatory protein (NF-kB) found in the cytoplasm of cells, which promotes HIV replication through binding to a viral regulatory gene sequence (LTR) [See, Osborn et al., *PNAS* 86:2336-2340 (1989)]. TNF in AIDS associated cachexia is suggested by elevated serum TNF and high levels of spontaneous TNF production in peripheral blood monocytes from patients [See, Wright et al., *J. Immunol.* 141(1):99-104 (1988)]. TNF in Bone Resorption Diseases, including arthritis, wherein it has been determined that when activated, leukocytes will produce a bone-reasorbing activity, and data suggests that TNF-a and TNF-β both contribute to this activity. [See e.g., Bertolini et al., *Nature* 319:516-518 (1986) and Johnson et al., *Endocrinology* 124(3):1424-1427(1489)] It has been determined that TNF stimulates bone resorption and inhibits bone formation in vitro and in vivo through stimulation of osteoclast formation and activation combined with inhibition of osteoblast function. Although TNF may be involved in may bone resorption disease, including arthritis, the most compelling link with disease is the association between production of TNF by tumor or host tissues and malignancy associated hypercalcemia [See, *Calci. Tissue Int. (US)* 46(Suppl.):S3-10 (1990)]. In Graft versus Host Reaction, increased serum TNF levels have been associated with major complication following acute allogenic bone marrow transplants [See, Holler et al., *Blood,* 75(4):1011-1016(1990)]; cerebral malaria, which is a lethal hyperacute neurological syndrome associated with high blood levels of TNF and is the most severe complication occuring in malaria patients. A form of experimental cerebral malaria (ECM) that reproduces some features of the human disease was prevented in mice by administration of an anti-TNF antibody. [See, Grau et al., *Imm. Review* 112:49-70 (1989)]. Levels of serum TNF correlated directly with the severity of diease and prognosis in patients with acute malaria attacks [See Grau et al., *N. Engl. J. Med.* 320(24):1586-11591 (1989)]. Another disease state in which TMF plays a role is the area of chronic Pulmonary Inflammatory Disease. The deposition of silica particules leads to silicosis, a disease of progressive respiratory failure caused by a fibrotic reaction. Antibody to TNF completly blocked the silica-induced lung fibrosis in mice See Piguet et al., *Nature,* 344:245-247

(1990)]. High levels of TNF production (in the serum and in isolated macrophages) have been demonstrated in animal models of silica and asbestos induced fibrosis [See Bissonnette et al., *Inflammation* 13(3):329–339 (1989)]. Alveolar macrophages from pulmonary sarcoidosis patients have also been found to spontaneously release massive quantities of TNF as compared with macrophages from normal donors [See Baughman et al., *J. Lab. Clin. Med.* 115(1):36–42 (1990)].; TNF is also implicated in another acute disease state such as the inflammatory response which follows reperfusion, called Reperfusion Injury and is a major cause of tissue damage after loss of blood flow. [See, Vedder et al., *PNAS* 87:2643–2646 (1990)]; TNF also alters the properties of endothelial cells and has vanous pro-coagulant activities, such as producing an increase in tissue factor procoagulant activity and suppression of the anticoagulant protein C pathway as well as down-regulating the expression of thrombomodulin [See, Sherry et al., *J. Cell Biol.* 107:11269–1277 (1988)]. TNF also has pro-inflammatory activities which together with its early production (during the intial stage of an inflammatory event) make it a likely mediator of tissue injury in several important disorders including but not limited to, myocardial infarction, stroke and circulatory shock. Of specific importance may be TNF-induced expression of adhesion molecules, such as intercellular adhesion molucule (ICAM) or endothelial leukocyte adhesion molecule (ELAM) on endothelial cells [See, Munro et al., *Am. J. Path.* 135(1):121–132 (1989)].

TNF is also believed to be an important mediator of many other inflammatory states or diseases. Therefor, inhibitors of TNF production would have utility in any inflammatory state or disease in which abnormal levels of TNF are produced. Abnormal levels of TNF constitute levels of 1) free (not cell bound) TNF, greater than or equal to 1 picogram per.ml; 2) any cell associated TNF; or 3) the presence of TNF MRNA above basal levels in cells or tissues in which TNF is produced. In addition, the present invention attributes many biological disease states noted herein to IL-1 activity. These disease states are also considered appropriate disease states of TNF activity and hence compounds of Formula (II) are also useful in their treatment as well, and should not be considered soley a limitation to IL-1 activity alone.

An effective, TNF production inhibiting amount of a compound of Formula (II) or a pharmaceutically acceptable salt thereof is useful in treating, prophylactically or therapeutically, any disease state in a human which is exacerbated or caused by excessive or unregulated TNF production by such human's monocytes and/or macrophages.

This invention relates to the use of a compound of Formula (II), or a pharmaceutically acceptable salt thereof in the manufacture of a medicament for the treatment of prophylactically or therapeutically, any disease state in a human which is exacerbated or caused by excessive or unregulated TNF production by such human's monocytes and/or macrophages.

This invention further relates to a compound of Formula (II) for use as a medicament in the treating, prophylactically or therapeutically, any disease state in a human which is exacerbated or caused by excessive or unregulated TNF production by such human's monocytes and/or macrophages.

This invention also relates to a pharmaceutical composition comprising an effective, non-toxic amount of a compound of Formula (IA) and a pharmaceutically acceptable carrier or diluent. The compounds of Formula (I) or (II) are administered in conventional dosage forms prepared by combining a compound of Formula (I) or (II) in an amount sufficient to produce IL-1 or TNF production inhibiting activity, respectively, with standard pharmaceutical carriers according to conventional procedures. These procedures may involve mixing, granulating and compressing or dissolving the ingredients as appropriate to the desired preparation.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl monostearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg. to about 1 g. When a liquid carrier is used, the preparation will be in the form of a syrup, emulsion, soft gelatin capsule, sterile injectable liquid such as an ampule or nonaqueous liquid suspension.

To obtain a stable water soluble dose form of an insoluble Formula (I) compound, a pharmaceutically acceptable salt of the Formula (I) or (II) compound is dissolved in an aqueous solution of an organic or inorganic acid, such as a 0.3M solution of succinic acid or, preferably, citric acid.

The method of the subject invention may be carried out by delivering the monokine activity interfering agent parenterally. The term 'parenteral' as used herein includes intravenous, intramuscular, subcutaneous intranasal, intrarectal, intravaginal or intraperitoneal administration. The subcutaneous and intramuscular forms of parenteral administration are generally preferred. Appropriate dosage forms for such administration may be prepared by conventional techniques.

A suitable dose of any TNF production inhibiting compound of a compound of Formula (II) administered parenterally will preferably be from about 1 to about 100 mg per kilogram (kg) of total body weight, most preferably from about 5 to about 80 mg/kg per day. A suitable IL-1 production inhibiting compound of Formula (I) administered parenterally will preferably be from about 1 to about 100 mg per kilogram (kg) of total body weight, preferably from about 5 to about 80mg/kg/day. Most preferably from about 3 to about 60 mg/k, per day. Preferably, each parenteral dosage unit will contain the active ingredient [i.e., the compound of Formula (I) or (II)] in an amount from about 50 mg. to about 500 mg.

The compounds of Formula (I) or Formula (II) may also be administered topically. Thus, the compounds of Formula (I) or Formula (II) may be administered topically in the treatment or prophylaxis of inflammatory topical disease states mediated or exacerbated by excessive IL-1 or TNF production, respectively, such as rheumatoid arthritis, rheumatoid spondylitis, osteoarthritis, gouty arthritis and other arthritic conditions, inflamed joints, eczema, psoriasis or other inflammatory skin conditions such as sunburn; inflammatory eye conditions including conjunctivitis; pyresis, pain and other conditions associated with inflammation.

The amount of a compound of Formula (I) or Formula (II) required for therapeutic effect on topical administration will, of course, vary with the compound chosen, the nature and severity of the inflammatory condition and the animal undergoing treatment, and is ultimately at the discretion of the physician. A suitable dose for anti-inflammatory activity for a compound of Formula (I) is 1 mg to 100 mg. A suitable dose of a compound of Formula (II) for anti-inflammatory activity is 1 mg to 1000 mg.

By topical administration is meant non-systemic administration and includes the application of a compound of Formula (I) or (II) externally to the epidermis, to the buccal cavity and instillation of such a compound into the ear, eye and nose, and where the compound does not significantly enter the blood stream. By systemic administration is meant oral, intravenous, intraperitoneal and intramuscular administration.

A suitable dose of an IL-1 production inhibiting compound of Formula (I) is 15 mg to 500 mg of base for topical administration, the most preferred dosage being 1 mg to 100 mg, for example, 5 to 25 mg administered two or three times daily. The daily topical dosage regimen will preferably be from about 2 mg to about 10 mg per site of administration.

A suitable dose of any TNF production inhibiting compound of Formula (II) is from about 1 mg to about 1000 mg of base for topical administration, the most preferred daily dosage being 15 mg to 500 mg, the single dosage range being about 5 mg to 160 mg. The daily topical dosage regimen will preferably be two or three times daily.

White it is possible for an active ingredient to be administered alone as the raw chemical, it is preferable to present it as a pharmaceutical formulation. The active ingredient may comprise, for topical administration, from 0.001% to 10% w/w, e.g. from 1% to 2% by weight of the formulation although it may comprise as much as 10% w/w but preferably not in excess of 5 % w/w and more preferably from 0.1% to 1% w/w of the formulation.

The topical formulations of the present invention comprise an active ingredient together with one or more acceptable carrier(s) therefor and optionally any other therapeutic ingredient(s). The carrier(s) must be 'acceptable' in the sense of being compatible with the other ingredients of the formulation and not deleterious to the recipient thereof. The present invention also relates to a pharmaceutical composition comprising an effective amount of a compound of Formula (I) or Formula (II) in a pharmaceutically acceptable carrier or diluent with an effective amount of one or more additional agents having IL-1 inhibitory activity, TNF inhibitory activity, cycloogenase inhibitory activity or 5-lipoxygenase inhibitory activity.

Formulations suitable for topical administration include liquid or semi-liquid preparations suitable for penetration through the skin to the site of inflammation such as liniments, lotions, creams, ointments or pastes, and drops suitable for administration to the eye, ear or nose.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified by filtration, transferred to a suitable container which is then sealed and sterilized by autoclaving or maintaining at 98°-100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as steric or oleic acid together with an alcohol such as prolylene glycol or macrogols. The formulation may incorporate any suitable surface active agent such as an anionic, cationic or non-ionic surfactant such as sorbitan esters or polyoxyethylene derivatives thereof. Suspending agents such as natural gums, cellulose derivatives or inorganic materials such as silicaceous silicas, and other ingredients such as lanolin, may also be included.

The compounds of Formula (I) or (II) may also be administered by inhalation. By "inhalation" is meant intranasal and oral inhalation administration. Appropriate dosage forms for such administration, such as an aerosol formulation or a metered dose inhaler, may be prepared by conventional techniques. The preferred daily dosage amount of a compound of Formula (I) administered by inhalation is from about 1 mg to about 1000 m, per day, preferably from about 1 mg to about 100 mg per day.

A suitable dose of any TNF production inhibiting compound of Formula (II) administered by inhalation is from about 1 mg to about 1000 mg per day. More preferably from about 10 mg to about 100 mg per day.

This invention also relates to a method of inhibiting the production of IL-1 by monocytes and/or macrophages in a human in need thereof which comprises administering an effective, IL-1 production inhibiting amount of a compound of Formula (I) or a pharmaceutically acceptable salt thereof to such human. A compound of Formula (I) or a pharmaceutically acceptable salt thereof can be administered to such human in a conventional dosage form prepared by combining a compound of Formula (I), or a pharmaceutically acceptable salt thereof, with a conventional pharmaceutically acceptable carrier or diluent according to known techniques, such as those described above as well as those described in Adams et al., U.S. Ser. No. 255,816 filed Oct. 11, 1988 the disclosure of which is hereby incorporated by reference. It will be recognized by one of skill in the art that the form and character of the pharmaceutically acceptable carrier or diluent is dictated by the amount of active ingredient with which it is to be combined, the route of administration and other well-known variables.

A compound of Formula (I) or a pharmaceutically acceptable salt thereof is administered to a human in need of inhibition of IL-1 production by its monocytes and/or macrophages in an amount sufficient to inhibit such excessive IL-1 production to the extent that it is regulated down to normal levels. A compound of Formula (II) or a pharmaceutically acceptable salt thereof is administered to a human in need of inhibition of TNF production by its monocytes and/or macrophages in an amount sufficient to inhibit such excessive TNF production to the extent that it is regulated down to normal levels.

The route of administration may be oral, parenteral or topical. The term parenteral as used herein includes intravenous, intramuscular, subcutaneous intranasal, intrarectal, intravaginal or intraperitoneal administration. The subcutaneous and intramuscular forms of parenteral administration are generally preferred.

As stated above, the method of the subject invention may be carried out by delivering the compounds of Formula (I) or (II) orally. Appropriate dosage forms for such administration may be prepared by conventional techniques. A suitable dose of a compound of Formula (I) or (II) for a daily oral dosage regimen will preferably be from about 1 to about 100 mg/kilogram of total body weight, more preferably from about 5 mg to 80 mg/kg.

The daily parenteral dosage regimen for a compound of Formula (I) or (II) will preferably be from about 2 to about 80 mg per kilogram (kg) of total body weight, most preferably from about 3 to about 60 mg/kg. The daily topical dosage regimen for a compound of Formula (I) or (II) will preferably be from about 2 mg to about 10 mg per site of administration. It will be recognized by one of skill in the art that the optimal quantity and spacing of individual dosages of a compound of Formula (I) or (II) or a pharmaceutically acceptable salt thereof will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of a compound of Formula (I) or a pharmaceutically acceptable salt thereof given per day for a defined number of days, can be ascertained by those skilled in the art using conventional course of treatment determination tests.

EXAMPLES

Without further elaboration, it is believed that one skilled in the art can, using the preceding description, utilize the present invention to its fullest extent. The following Examples are, therefore, to be construed as merely illustrative and not a limitation of the scope of the present invention in any way.

PHARMACEUTICAL COMPOSITION EXAMPLES

Example A—Capsule Composition

A pharmaceutical composition of this invention in the form of a capsule is prepared by turning a standard two-piece hard gelatin capsule with 50 mg. of a compound of Formula (IA), in powdered form, 110 mg. of lactose, 32 mg. of talc and 8 mg. of magnesium stearate.

Example B—Injectable Parenteral Composition

A pharmaceutical composition of this invention in a form suitable for administration by injection is prepared by stirring 1.5% by weight of a compound of Formula (IA) in 10% by volume propylene glycol and water. The solution is sterilized by filtration.

Example C—Ointment Composition

Compound of Formula (IA) 1.0 g
White soft paraffin to 100.0 g

The compound of Formula (IA) is dispersed in a small volume of the vehicle and this dispersion is gradually incorporated into the bulk to produce a smooth, homogeneous product which is filled into collapsible metal tubes.

Example D—Topical Cream Composition

Compound of Formula (IA) 1.0 g
Polawax GP 200 20.0 g
Lanolin Anhydrous 2.0 g
White Beeswax 2.5 g
Methyl hydroxybenzoate 0.1
Distilled Water to 100.0 g The polawax, beeswax and lanolin are heated together at 60° C. and added to a solution of methyl hydroxybenzoate. Homogenization is achieved using high speed stirring and the temperature is allowed to fall to 50° C. The compound of Formula (IA) is added and dispersed throughout, and the composition is allowed to cool with slow speed stirring.

Example E—Topical Lotion Composition

Compound of Formula (IA) 1.0 g
Sorbitan Monolaurate 0.6 g
Polysorbate 20 0.6 g
Cetostearyl Alcohol 1.2 g
Glycerin 6.0 g
Methyl Hydroxybenzoate 0.2 g
Purified Water B.P. to 100.00 ml The methyl hydroxybenzoate and glycerin are dissolved in 70 ml of the water at 75° C. The sorbitan monolaurate, polysorbate 20 and cetostearyl alcohol are melted together at 75° C. and added to the aqueous solution. The resulting emulsion is homogenized, allowed to cool with continuous stirring and the compound of Formula (IA) is added as a suspension in the remaining water. The whole suspension is stirred until homogenized.

Example F—Eye Drop Composition

Compound of Formula (IA) 0.5 g
Methyl Hydroxybenzoate 0.01 g
Propyl Hydroxybenzoate 0.04 g
Purified Water B.P. to 100.00 ml The methyl and propyl hydroxybenzoates are dissolved in 70 ml purified water at 75° C. and the resulting solution is allowed to cool. The compound of Formula (IA) is then added, and the solution is made up to 100 ml with purified water. The solution is sterilized by filtration through a membrane filter (0.22 mu m pore size) and packed aseptically into suitable sterile containers.

Example G—Composition for Administration by Inhalation

For an aerosol container with a capacity of 15-20 ml: Mix 10 mg of a compound of Formula (IA) with 0.1-0.2% of a lubricating agent, such as Span 85 or oleic acid, and disperse such mixture in a propellant (c.a.), such as freon, preferably a combination of freon 114 and freon 12, and put into an appropriate aerosol container adapted for either intranasal or oral inhalation administration.

Example H—Composition for Administration by Inhalation

For an aerosol container with a capacity of 15-20 ml: Dissolve 10 mg of a compound of Formula (IA) in ethanol (6-8 ml), add 0.1-0.2% of a lubricating agent, such as Span 85 or oleic acid, and disperse such in a propellant (c.a.), such as freon, preferably a combination of freon 144 and freon 12, and put into an appropriate aerosol container adapted for either intranasal or oral inhalation administration.

UTILITY EXAMPLES

In Tables 1 and 2 of the following Utility Examples, the following abbreviations are employed:

| ABBREVIATION | FORMULA (I) COMPOUND |
|---|---|
| Compound 1 | 2-(4-methylthiophenyl)-3-(4-pyridyl)-6,7-dihydro-[5H]-pyrrolo-[1,2-a-]-imidazole. |
| Compound 2 | 2-(4-methylsulfinylphenyl)-3-(4-pyridyl)-6,7-dihydro-[5H]-pyrrolo-[1,2-a]-imidazole. |
| Compound 3 | 2-(4-ethylthiophenyl)-3-(4-pyridyl)-6,7-dihydro-5H]-pyrrolo-[1,2-a]-imidazole. |
| Compound 4 | 2-(4-ethylsulfinylphenyl)-3-(4-pyridyl)-6,7-dihydro-5H]-pyrrolo-[1,2-a-]-imidazole. |
| Compound 5 | 2-(4-methylthiophenyl)-3-(4-(2-methyl)pyridyl)-6,7-dihydro-[5H]-pyrrolo-[1,2-a-]-imidazole |
| Compound 6 | 2-(4-methylsulfinylphenyl)-3-(4-(2-methyl)-pyridyl)-6,7-dihydro-[5H]-pyrrolo-[1,2-a]-imidazole. |
| Compound 7 | 2-(4-methoxyphenyl)-3-(4-pyridyl)-imidazo-[1,2-a]-pyridine. |
| Compound 8 | 5-(3,4-(methylenedioxy)phenyl)-6-(4-pyridyl)-2,3-dihydroimidazo-[2-1-b]-thiazole. |
| Compound 9 | 2-(4-methoxyphenyl)-3-(4-(2-methyl)pyridyl)-6,7-dihydro-[5H]-pyrrolo-[1,2-a]-imidazole. |
| Compound 10 | 2-(4-acetoxymethylthiophenyl)-3-(4-pyridyl)-6,7-dihydro-[5H]-pyrrolo-[1,2-a]-imidazole. |
| Compound 11 | 6-(4-methylthiophenyl)-5-(4-pyridyl)-2,3-dihydro-imidazo-[2,1-b]-thiazole. |
| Compound 12 | 5-(4-methylthiophenyl)-6-(4-pyridyl)-2,3-dihydro-imidazo-[2,1-b]-thiazole. |
| Compound 13 | 3-(4-methylthiophenyl)-2-(4-pyridyl)-6,7-dihydro-[5H]-pyrrolo-[1,2-a]-imidazole. |
| Compound 14 | 2-(4-propylthiophenyl)-3-(4-pyridyl)-6,7-dihydro-[5H]-pyrrolo-[1,2-a]-imidazole. |
| Compound 15 | 2-(4-methylthiophenyl)-3-(4-(2-ethyl)pyridyl)-6,7-dihydro-[5H]-pyrrolo-[1,2-a-]-imidazole. |

EXAMPLE A

Inhibitory Effect of compounds of Formula (I) on in vitro IL-1 Production by Human Monocytes The effects of compounds of Formula (I) on the in vitro production of IL-1 by human monocytes was examined using the following protocol.

Bacterial lipopolysaccharide (LPS) was used to induce IL-1 production by human peripheral blood monocytes. IL-1 activity was measured by its ability to stimulate a Interleukin 2 (IL-2) producing cell line (IL-4) to secrete IL-2, in concert with A23187 ionophore, according to the method of Simon et al., J. Immunol. Methods, 84, 85, (1985). Human peripheral blood monocytes were isolated and purified from either fresh blood preparations from volunteer donors, or from blood bank buffy coats, according to the procedure of Colotta et al., J. Immunol., 132, 936 (1984). $1 \times 10^6$ of such monocytes were plated in 24-well plates at a concentration of 1-2 million/ml per well. The cells were allowed to adhere for 2 hours, after which time non-adherent cells were removed by gentle washing. Test compounds were then added to the cells for 1 hour (hr) before the addition of lipopolysaccharide (50 ng/ml), and the cultures were incubated at 37° C. for an additional 24 hours. At the end of the incubation period, culture supernatants were removed and clarified of cells and all debris. Culture supernatants were immediately assayed for IL-1 biological activity in the manner described above, as well as for prostaglandin and/or leukotriene concentrations by radioimmunoassay.

The results indicated that human peripheral blood monocytes are exquisitely sensitive to bacterial endotoxin. Nanogram or even picogram quantities of LPS stimulated high levels of IL-1 production as well as prostaglandin production; however, little, if any, leukotriene was detected in such supernatants. These observations are consistent with previous reports [(See, Humes et al., J. Biol. Chem., 257, 1591 (1982)].

The results of the effects of compounds of Formula (I) on the in vitro IL-1 production by human monocytes is reported in Table 1. As shown in Table 1, compounds of Formula (I), other than those compounds wherein R is a sulfinyl derivative, are potent inhibitors of in vitro IL-1 production by human monocytes. As shown in Table 1, the sulfinyl derivatives are not active in the in vitro assay. In fact, the sulfinyl derivatives of Formula (I) possess no known biological activity in any in vitro assay. However, the sulfinyl derivatives function as predrugs to their corresponding sulfide, i.e., they function in vivo to inhibit the production of IL-1 because they are metabolized so that they are reductively converted, in vivo, to their corresponding biologically active alkylthio or alkenylthio form. Proof of this in vivo conversion of the sulfinyl derivatives to a biologically active form is indicated by the antiinflammatory activity of the sulfinyl compounds in the in vivo assay described in Table 2.

TABLE 1

EFFECT OF COMPOUNDS OF FORMULA (I) ON LPS-STIMULATED IL-1 PRODUCTION BY HUMAN MONOCYTES[b]

| COMPOUND NUMBER | IC$_{50}$ (μM) |
|---|---|
| 1 | 2.0 |
| 2 | NA[a] |
| 3 | 2.0 |
| 4 | NA |
| 5 | 2.7 |
| 6 | NA |
| 7 | 1.0 |
| 8 | 10.0 |
| 9 | 0.7 |
| 10 | 6.3 |
| 11 | 1.8 |
| 12 | 1.8 |
| 13 | 2.0 |
| 14 | >10.0 |

TABLE 1-continued
EFFECT OF COMPOUNDS OF FORMULA (I) ON LPS-STIMULATED IL-1 PRODUCTION BY HUMAN MONOCYTES[b]

| COMPOUND NUMBER | IC$_{50}$ ($\mu$M) |
|---|---|
| 15 | 1.3 |

[a]NA means not active
[b]IL-1 activity was assayed as described above, i.e., by culturing EL4 cells with dilutions of supernatant from monocytes and subsequently culturing EL4 supernatants on a IL-2 dependent cell line.

TABLE 2
ANTIINFLAMMATORY ACTIVITY OF THE SULFINYL DERIVATIVES OF FORMULA (I)

| COMPOUND NUMBER (50 mg/kg p.o.) | PERCENT INHIBITION OF ARACHIDONIC ACID-INDUCED MOUSE EAR SWELLING[a] |
|---|---|
| 1 | 56***[b] |
| 2 | 44*** |
| 3 | 56*** |
| 4 | 41*** |
| 5 | 59*** |
| 6 | 59*** |

[a]Mouse ear edema was measured as described in Griswold et al., Inflammation, 11(2), 189-199 (1987), the disclosure of which is hereby incorporated by reference.
[b]***indicates statistical significance at a p less than 0.001

The exact mechanism by which any compound of Formula (I) inhibits in vitro IL-1 production by monocytes is not presently known.

The data in Table 1 show that compounds of Formula (I) inhibit IL-1 production by human monocytes in vitro. This inhibitory activity does not seem to correlate with the property of any of the compounds of Formula (I) in mediating arachidonic acid metabolism inhibition since other nonsteroidal antiinflammatory drugs with potent cyclooxygenase and/or lipoxygenase inhibitory activity do not inhibit IL-1 production at nontoxic doses. Furthermore, the ability of a compound to inhibit production of prostaglandin and/or leukotriene synthesis does not mean that it will necessarily also inhibit IL-1 production.

Based on the widely held belief of the role of unmodulated (i.e., excessive) in vivo IL-1 production in causing or aggravating inflammatory responses and other disease states (see, e.g., Fontana et al., supra; Wood et al., supra; Akejima and Dinarello, supra; Habicht and Beck, supra; Chesque et al., supra; Benjamin et al., supra; and Dinarello, supra), and based on the fact that compounds of Formula (I) inhibit in vitro IL-1 production by human macrophages and/or monocytes (see, Table 1), or are converted in vivo to their biologically active form (see, Table 2), all compounds of Formula (I) will inhibit the in vivo IL-1 production by monocytes and/or macrophages in a human in need thereof when used according to the method of the subject invention.

The inhibitory action of IL-1 activity has not been found to correlate with arachidonic acid metabolism for the compounds of Formula (I). This further substantiates the unpredictable nature of the compounds of Formula (I) for possessing either IL-1.

In Table 3 the following additional compound abbreviations employed are:

| Compound 16 | 2-[Trimethylacetyl(thiophenyl)]-3-(4-pyridyl)-6,7-dihydro[5H]pyrrolo-[1,2-a]-imidazole. |
|---|---|
| Compound 17 | 2-(4-(2-Propoxy)phenyl)-3-(4-pyridyl)-6,7-dihydro-[5H]-pyrrolo-[1,2-a]-imidazole. |
| Compound 18 | 2-(4-(1-Ethoxy)phenyl)-3-(4-pyridyl)-6,7-dihydro[5H]pyrrolo-[1,2-a]-imidazole. |
| Compound 19 | 2-(4-(1-Propoxy)phenyl)-3-(4-pyridyl)-6,7-dihydro[5H]pyrrolo-[1,2-a]-imidazole. |
| Compound 20 | 2-(Acetyl-thio-phenyl)-3-(4-pyridyl)-6,7-dihydro[5H]-pyrrolo-[1,2-a]-imidazole. |
| Compound 21 | 2-(4-Methoxyphenyl)-3-(4-pyridyl)-6,7-dihydro-[5H]-pyrrolo-[1,2-a]-N-methylimidazole, monomethylsulfate. |
| Compound 22 | 2-Phenyl-3-(4-pyridyl)-6,7-dihydro-[5H]-pyrrolo-[1,2-a]imidazole. |
| Compound 23 | 2-(4-Mercaptophenyl)-3-(4-pyridyl)-6,7-dihydro-[5H]-pyrrolo-[1,2-a]-imidazole disulfide. |
| Compound 24 | 2-(4-Methoxyphenyl)-3-(4-pyridyl)-6,7-dihydro-[5H]-pyrrolo-[1,2-a]-imidazole. |
| Compound 25 | 6-(4-Methoxyphenyl)-5-(4-pyridyl)-2,3-dihydroimidazo-[2,1-b]-thiazole. |
| Compound 26 | 5-(4-Methoxyphenyl)-6-(4-pyridyl)-2,3-dihydroimidazole-[2,1-b]-thiazole. |
| Compound 27 | 2-(4-Bromophenyl)-3-(4-pyridyl)-6,7-dihydro-[5H]-pyrrolo-[1,2-a]-imidazole. |

TABLE 3
Inhibition of IL-1 production by LPS stimulated monocytes in vitro

| Compound Number | IC$_{50}$ (mM) |
|---|---|
| 16 | NA |
| 17 | NA |
| 18 | 10 |
| 19 | NA |
| 20 | NA |
| 21 | NA |
| 22 | 0.5 |
| 23 | 5.9 |
| 24 | 0.1 |
| 25 | 3.0 |
| 26 | $\geq$ 10 |
| 27 | 0.7 |

NA = essentially considered not active at 10 mM

UTILITY EXAMPLE FOR INHIBITION OF THE PRODUCTION OF TNF

Example A

Two models of endotoxin shock have been utilized to determine in vivo TNF activity and are described below. The actual protocol used in the models is described in Utility Model Examples A and B set out below, i.e. P. acnes model and LPS-GAL model. In these models protection from the lethal effects of endotoxin shock is provided by the compound 2-(4-methyl-sulfoxyphenyl)-3-(4-pyridyl)-6,7-dihydro(5H)-pyrrolo-[1,2-a]-imidazole (herein called Compound A). The data in FIGS. 1–5 clearly demonstrates the ability of Compound 1 to reduce the in vivo level of tumor necrosis factor (TNF).

Figure 2:
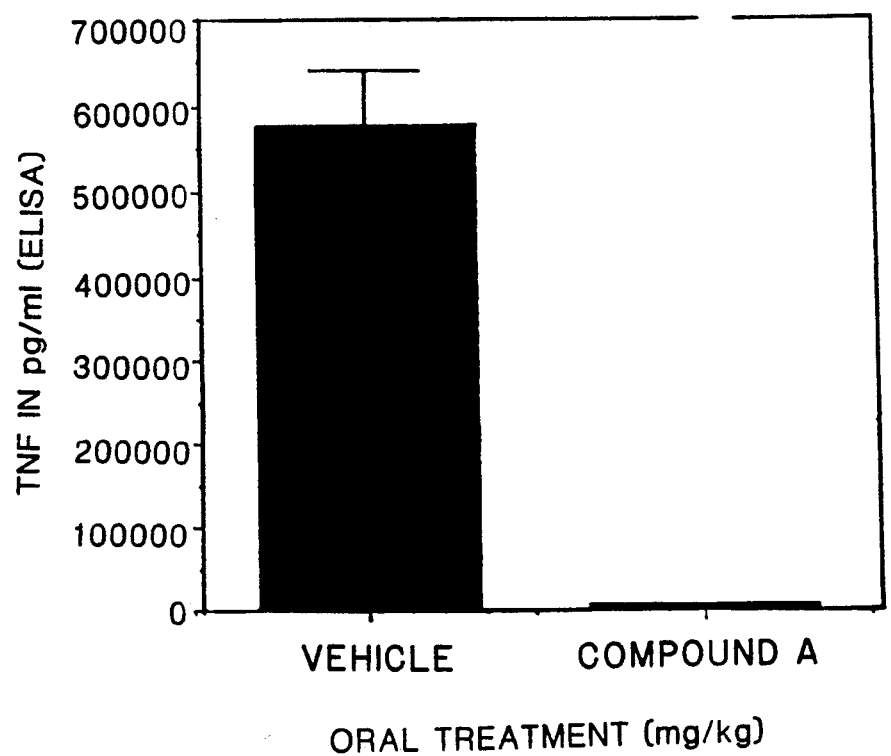

Compound 1 shows a reduction in serum TNF levels in the P acnes/LPS treated mice model as depicted by the data shown in FIG. 1, which demonstrates decreased levels of in vivo TNF relative to increased oral dosage of Compound A. FIG. 2 demonstrates inhibition of TNF production, also in the P. acnes/LPS Model for Compound A.

Figure 3:
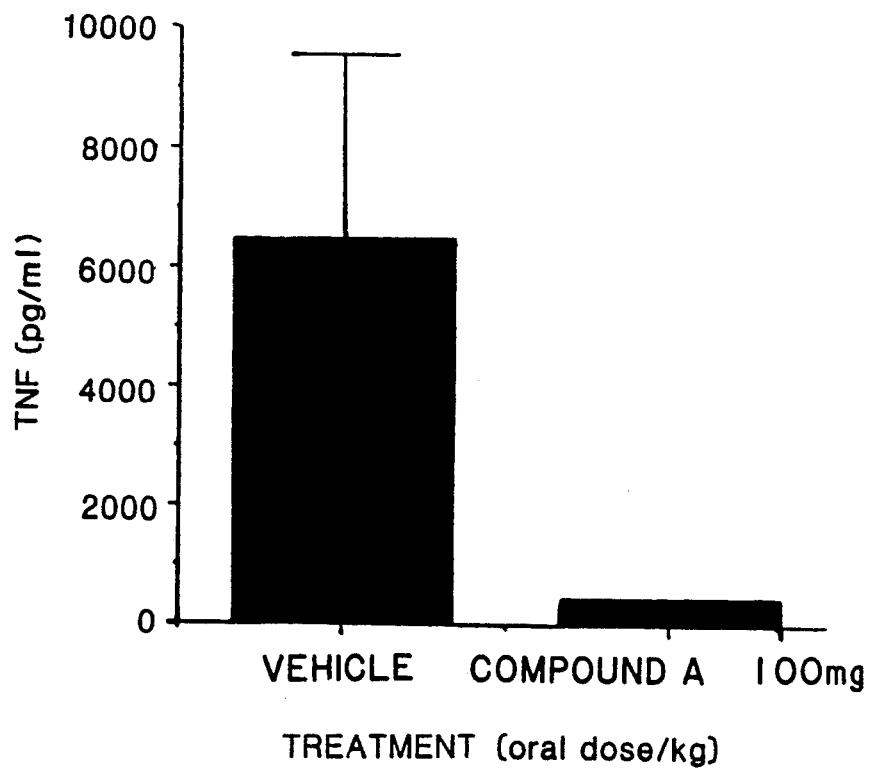
Figure 4:
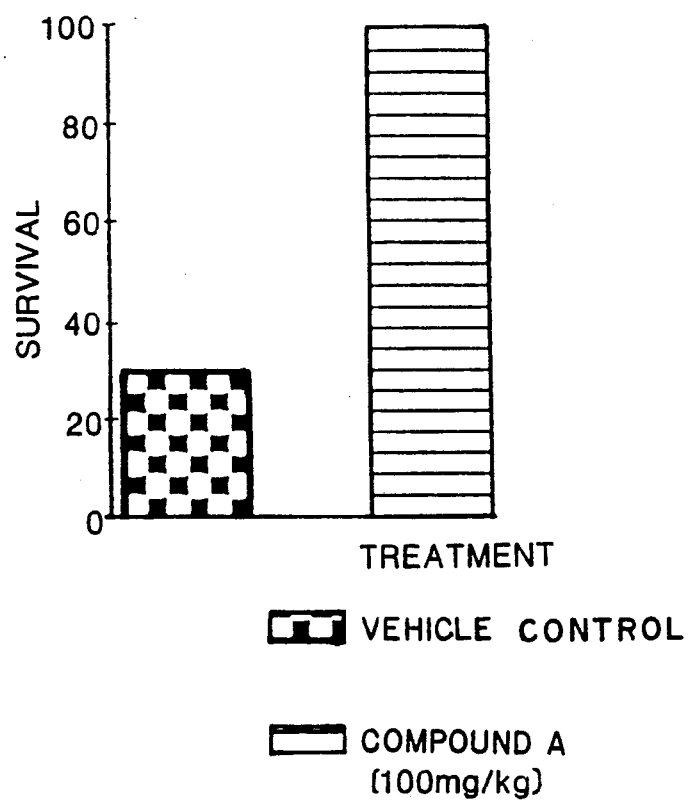

FIG. 3 shows a reduction of serum TNF levels at 100 mg/kg for Compound A in the LPS-GAL Model. FIG. 4 demonstrates 100% survival rate of the animals with endotoxic shock in the LPS-GAL model after treatment with Compound A compared to only a 30% survival rate of the animals in the control group.

It has also been determined, using one or both of the in vivo assays described herein, that 2-(4-Ethylsulfinylphenyl)-3-(4-pyridyl)-6,7-dihydro-[5H]-pyrrolo-[1,2-a]- imidazole, 2-(4-methylthiophenyl)-3-[4-(2-methyl-pyridyl)]-6,7-dihydro-[5H]-pyrrolo-[1,2-a]-imidazole, and 6-(4-Fluorophenyl)-5-(4-pyridyl)-2,3-dihydroimidazo[2,1-b]thiazole-1,1-dioxide also inhibited in vivo TNF levels as well as protected the animals from endotoxic induced shock.

The data shown herein demonstrate that the compounds of the present invention inhibit TNF production in a mammal. Therefore, the compounds of the present invention are useful as monolone activity interfering agents, e.g. they are useful in inhibiting the production of tumor necrosis factor (TNF) by monocytes or macrophages in a human.

UTILITY EXAMPLE MODEL A

Endotoxin Shock in D-gal-Sensitized Mice

The protocol used to test the compound of the method of the subject invention was essentially as has been described in Galanos et al., *Proc. Nat'l Acad. Sci USA*, 76:5939-43 (1979) whose disclosure is herein incorporated by reference. Briefly, D-gal (D(+) Galactosidase) sensitizes various strains of mice to the lethal effects of endotoxin. The administration of D-gal (300-500 mg/kg) intravenously (i.v.) sensitizes the mice to doses of Lipopolysaccharide(LPS) as low as 0.1 mg. Briefly, male C57BL/6 mice, obtained from Charles River Laboratories (Stone Ridge, N.Y., USA) of 6-12 weeks of age were injected i.v. with 0.1 mg of LPS from *Salmonella typhosa* (Difco Laboratories, Detroit, Mich., USA) admixed with D(+)-gal (Sigma; 500 mg/kg) in 0.20-0.25 ml pyrogen-free saline. Compounds to be tested were administered at various times prior to or following the i.v. injection of LPS/D-gal. In this model, the control animals usually die 5-6 hr. following the injection of LPS, although on occasion deaths are seen between 24 and 48 hr.

UTILITY MODEL EXAMPLE B

Endotoxin Shock in *P. acnes*-Sensitized Mice

This model is a modification of the previously described protocol for the in vivo induction of TNF as described in Haranaka et al., *Cancer Immunol Immunother.* 18:81-90, (1984). Treatment with Proprionibacterium Acnes (*P. acnes*) (1 mg/animal i.p.) renders mice susceptible to the lethal effects of LPS injected 10 days later.

*P. acnes* was purchased from Burroughs Wellcome (Triangle Park, N.C., USA), and 1 microgram (ug) of the heat-killed bacteria was administered in 0.5 ml pyrogen-free saline by intraperitoneal (i.p.) injection to male C57BL/6 mice, obtained from Charles River Laboratories (Stone Ridge, N.Y., USA) of 6-12 weeks of age. Ten days later, the mice were injected i.v. with 1 mg LPS in 0.25 ml saline. Compounds to be tested were administered at various times prior to or following the injection of LPS. The survival of animals was monitored for 1 week.

Measurement of TNF Activity

Plasma levels of TNF were measured using a modification of the basic sandwich ELISA method described in Winston et al., *Current Protocols in Molecular Biology*, Pg. 11.2.1, Ausubel et al., Ed. (1987) John Wiley and Sons, New York, USA. The Elisa employed a hampster monoclonal anti-mouse TNF (Genzyme, Boston, Mass., USA) as the capture antibody and a polyclonal rabbit anti-murine TNF (Genzyme, Boston, Mass., USA) as the detecting antibody. TNF levels in rat samples were calculated from a standard curve generated with recombinant murine TNF (Genzyme, Boston, Mass., USA). TNF levels determined by ELISA correlated with levels detected by the L929 bioassay of Ruff et. al., *J. Immunol.* 125:1671-1677 (1980), with 1 Unit of activity in the bioassay corresponding to 70 picograms (pg) of TNF in the ELISA. The ELISA detected levels of TNF down to 25 pg/ml.

UTILITY EXAMPLES

In the following Table B of the Utility Examples, the following abbreviations are employed:

| ABBREVIATION | FORMULA (I) COMPOUNDS |
|---|---|
| Compound A | 2-(4-Methylsulfinylphenyl)3-(4-pyridyl)-6,7-dihydro[5H]-pyrrolo-[1,2-a]imidazole; |
| Compound B | 2-(4-methylthiophenyl)-3-(4-pyridyl)-6,7-dihydro-[5H]-pyrrolo[1,2-a]-imidazole; |
| Compound C | 2-phenyl-3-pyridyl-6,7-dihydro-[5H]-pyrrolo[1,2-a]imidazole; |
| Compound D | 2-p-bromophenyl-3-pyridyl-6,7-dihydro-[5H]-pyrrolo-[1,2-a]-imidazole; |
| Compound E | 2-(4-Methoxyphenyl)-3-(4-pyridyl)-7-oxo-5,6-dihydro-7-H-pyrrolo-[1,2-a]imidazole; |
| Compound F | 5,6-dihydro-2-(4-methoxyphenyl)-3-(4-pyridinyl)-[7H]-pyrrolo[1,2-a]-imidazole-7-ol; |
| Compound G | 2-(4-Acetoxymethylthiophenyl)-3-(4-pyridyl)-6,7-dihydro[5H]pyrrolo-[1,2-a]-imidazole; |
| Compound H | 2-(4-Methoxyphenyl)-3-(4-pyridyl)-6,7-dihydro-[5H]-pyrrolo-[1,2-a]imidazole; |
| Compound I | 6-(4-Fluorophenyl)-5-(4'-pyridyl)-2,3-dihydroimidazo[2,1-b]thiazole-1-oxide; |
| Compound J | 6-(4-Fluorophenyl)-5-(4-pyridyl)-2,3-dihydroimidazo[2,1-b]thiazole-1,1-dioxide; |
| Compound K | 2-(4-Ethylsulfinylphenyl)-3-(4-pyridyl)-6,7-dihydro[5H]pyrrolo-[1,2-a]-imidazole; |
| Compound L | 2-(4-Methylthiophenyl)-3-[4-(2-methyl-pyridyl)]-6,7-dihydro[5H]pyrrolo-[1,2-a]imidazole. |
| Compound M | 2-(4-Fluorophenyl)-3-(4-pyridyl)-6,7-dihydro-[5H]-pyrrolo-[1,2-a]-imidazole. |
| Compound N | 3-(4-Fluorophenyl)-2-(4-pyridyl)-6,7-dihydro-[5H]-pyrrolo-[1,2-a]-imidazole. |

EXAMPLE A

Inhibitory Effect of Compounds on in vitro TNF Production by Human Monocytes

The effects of the compounds enumerated above on the in vitro production of TNF by human monocytes was examined using the following protocol.

Bacterial lipopolysaccharide (LPS) was used to induce TNF production by human peripheral blood monocytes. TNF activity was measured by a modification of Winston et al., ELISA, described below. Human peripheral blood monocytes were isolated and purified from either fresh blood preparations from volunteer donors, from blood bank buffy coats, or from plateletpheresis residues according to the procedure of Colotta et al., *J. Immunol.*, 132, 936 (1984). $1 \times 10^6$ of such monocytes were plated in 24-well plates at a concentration of 1-2 million/ml per well. The cells were allowed to adhere for 2 hours, after which time non-adherent cells were removed by gentle washing. Test compounds were then added to the cells for 1 hour (hr) before the addition of LPS (50 ng/ml), and the cultures were incubated at 37° C. for an additional 24 hours. At the end of the incubation period, culture supernatants were removed and clarified of cells and all debris. Culture supernatants were immediately assayed for TNF levels in the manner described below.

Measurement of Human TNF

Levels of TNF were measured using a modification of the basic sandwich ELISA assay method described in Winston et al., *Current Protocols in Molecular Biology*, Page 11.2.1, Ausubel et al., Ed. (1987) John Wiley and Sons, New York, USA. The Elisa employes a murine monoclonal anti-human TNF antibody, described below, as the capture antibody and a polyclonal rabbit anti-human TNF, described below, as the second antibody. For detection, a peroxidase-conjgated goat anti-rabbit antibody (Boehringer Mannheim, Indianapolis, Ind., USA, Catalog #605222) was added followed by a substrate for peroxidase (1 mg/ml orthophenylenediamine with 0.1% urea peroxide). TNF levels in samples were calculated from a standard curve genereated with recombinant human TNF produced in *E. Coli* (obtained from SmithKIine Beecham Pharmaceuticals, King of Prussia, Pa., USA).

Production of Anti-Human TNF Antibodies

Monoclonal antibodies to human TNF were prepared from spleens of BALB/c mice immunized with recombinant human TNF using a modification of the method of Kohler and Millstein, *Nature* 256:495 (1975), the entire disclosure of which is hereby incorporated by reference. Polyclonal rabbit anti-human TNF antibodies were prepared by repeated immunization of New Zeland White (NZW) rabbits with recombinant human TNF emulsified in complete Freund's adjuvant (DEFCO, Ill., USA).

The results indicated that human peripheral blood monocytes are exquisitely sensitive to bacterial endotoxin. Nanogram or even picogram quantities of LPS stimulated high levels of TNF production as well as for IL-1 production.

The results of the effects of compounds on the in vitro TNF production by human monocytes are reported in Table B. The compounds wherein the phenyl substituent group of the pyrrolo(2,1-b]imidazoles and the dihydroimidazo [2,1-a] thiazoles of the present invention are not a sulfinyl derivatives, are potent inhibitors of in vitro TNF production by human monocytes. The compounds wherein the substituent is a sulfinyl derivatives are not active in the in vitro assay. However, the sulfinyl derivatives function as predrugs to their corresponding sulfide, i.e., they function in vivo to inhibit the production of TNF, because they are metabolized so that they are reductively converted, in vivo, to their corresponding biologically active alkylthio or alkenylthio form. Proof of this in vivo conversion of the sulfinyl derivatives to a biologically active form is indicated by the in vivo activity of the sulfinyl compounds in the in vivo assay described in Utility Models Examples A and B for Compound 2. The conversion of the sulfinyl/sulfoxy pro-drug derivatives to their active sulfinyl strucutre also holds true for IL-1 activity and is shown herein.

The results of the compounds of Formula (H) on the in vitro TNF production by human monocytes are reported in Table B. In Table B, NA=not active.

TABLE B

| LPS induced TNF Human Monocyte data | |
|---|---|
| Compound No. | IC$_{50}$ (mM) |
| A (Sulfinyl derivative) | NA |
| B (Thio derivative) | 1.0 |
| C | 0.8 |
| D | 1.0 |
| E | 1.0 |
| F | 1.0 |
| G | 3.0 |
| H | 0.5 |
| I | 0.2 |
| J | 9.0 |
| K | 7.0 |
| L | 7.0 |
| M | 0.2 |
| N | 1.0 |

SYNTHESIS EXAMPLES

As more elaborately described herein, all of the compounds of Formulas (C), (D), (E), (F) and (G) are useful as intermediates in the preparation of the compounds of Formula (IA). Additionally, as more elaborately described herein, while all of the compounds of Formula (IA) are useful in the method of the subject invention, some of the compounds of Formula (IA) are also useful as intermediates for preparation other compounds of Formula (IA).

As used herein in the Synthesis Examples, the term "Formula (A)" refers to a compound of the formula:

FORMULA (A)

wherein:
X is chosen from a group consisting of mono or disubstituted phenyl, 4-pyridyl and mono-C$_{1-4}$ alkyl-substituted-4-pyridyl; and
X$_1$ is a halogen such as Cl or Br.

As used herein in the Synthesis Examples, the term "Formula (B)" refers to a compound of the formula:

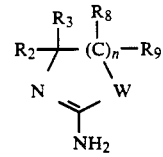

FORMULA (B)

W is —(CR$_4$R$_5$)—(CR$_6$R$_7$)—, —(NR$_4$)—(CR$_6$R$_7$)—, S(O)$_m$ or O;
m is 0; and
n is 1 or 2;
provided that:
(A) when W is —(CR$_4$R$_5$)—(CR$_6$R$_7$)— or —(NR$_4$)—(CR$_6$R$_7$)— and n is 1; R$_2$, R$_8$ and R$_4$, R$_6$ together represent two C═C bonds to form an aromatic pyridine ring or an aromatic pyridine ring; R$_3$, R$_5$, R$_7$ and R$_9$ are H or one or more of R$_3$, R$_5$, R$_7$ and R$_9$ are independently selected from H or C$_{1-2}$ alkyl;
(B) when W is S(O)$_m$ or O, m is 0 and n is 1; R$_3$ and R$_9$ are H or one or more of R$_3$ and R$_9$ are independently selected from H or C$_{1-2}$ alkyl; R$_2$, R$_8$ forms a C=C bond in an aromatic thiazole or oxazole ring; or (C) when W is S(O)$_m$, m is 0, and n is 1 or 2; R$_2$, R$_3$, R$_8$ and R$_9$ are H or one or more of R$_2$, R$_3$, R$_8$ and R$_9$ are independently selected from H or C$_{1-2}$ alkyl.

As used herein in the Synthesis Examples, the term "Formula (Ib)" refers to a compound of the formula:

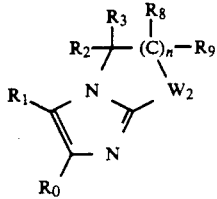

FORMULA (Ib)

wherein:
W$_2$ is —(CR$_4$R$_5$)—(CR$_6$R$_7$)—, —(NR$_4$)—(CR$_6$R$_7$)—, S(O)$_m$ or O;
m is 0;
n is 1 or 2; and
One of R$_1$ or R$_0$ is 4-pyridyl and the other is selected from:
(a) monosubstituted phenyl wherein said substituent is selected from C$_{1-3}$ alkylthio, C$_{1-2}$ alkoxy, halo, H, or C$_{1-4}$ alkyl; or
(b) disubstituted phenyl wherein said substitutents are independently selected from C$_{1-3}$ alkylthio, C$_{1-2}$ alkoxy, halo, C$_{1-4}$ alkyl, or the disubstituents together form a methylene dioxy group;
provided that:
(A) when W$_2$ is —(CR$_4$R$_5$)—(CR$_6$R$_7$)— or —(NR$_4$)—(CR$_6$R$_7$)— and n is 1; R$_2$, R$_8$ and R$_4$, R$_6$ together represent two C=C bonds to form an aromatic pyridine ring or an aromatic pyrimidine ring; R$_3$, R$_5$, R$_7$ and R$_9$ are H or one or more of R$_3$, R$_5$, R$_7$ and R$_9$ are independently selected from H or C$_{1-2}$ alkyl; or
(B) when W$_2$ is S(O)$_m$, m is 0, and n is 1 or 2; R$_2$, R$_3$, R$_8$ and R$_9$ are H or one or more of R$_2$, R$_3$, R$_8$ and R$_9$ are independently selected from H or C$_{1-2}$ alkyl; or
(C) when W$_2$ is S(O)$_m$ or O, m is 0 and n is 1; R$_3$ and R$_9$ are H or one or more of R$_3$ and R$_9$ are independently selected from H or C$_{1-2}$ alkyl; R$_2$, R$_8$ forms a C=C bond in an aromatic thiazole or oxazole ring.

As used herein in the Synthesis Examples, the term "Formula (Ic)" refers to a compound of the formula:

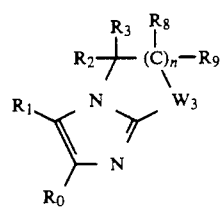

FORMULA (Ic)

wherein:
W$_3$ is —(CR$_4$R$_5$)—(CR$_6$R$_7$)—, —(NR$_4$)—(CR$_6$R$_7$)—, S(O)$_m$ or O;
m is 0 or 2;
n is 1 or 2;
one of R$_1$ or R$_0$ is 4-pyridyl or mono-C$_{1-4}$alkyl-substituted-4-pyridyl, provided that when R$_1$ is mono-C$_{1-4}$alkyl-substituted-4-pyridyl the mono-C$_{1-4}$alkyl substituent is located at the 2-position of the pyridine ring, and the other of R$_1$ or R$_0$ is selected from:
(a) monosubstituted phenyl wherein said substituent is C$_{1-3}$ alkylsulfinyl; or
(b) disubstituted phenyl wherein one of said substituents must be C$_{1-3}$ alkylthio and the other is selected from C$_{1-3}$ alkylsulfinyl, C$_{1-2}$ alkoxy, halo, or C$_{1-4}$ alkyl;
provided that:
(A) when W$_3$ is —(CR$_4$R$_5$)—(CR$_6$R$_7$)— or —(NR$_4$)—(CR$_6$R$_7$)— and n is 1; R$_2$, R$_8$ and R$_4$, R$_6$ together represent two C=C bonds to form an aromatic pyridine ring or an aromatic pyrimidine ring; R$_3$, R$_5$, R$_7$ and R$_9$ are H or one or more of R$_3$, R$_5$, R$_7$ and R$_9$ are independently selected from H or C$_{1-2}$ alkyl; or
(B) when W$_3$ is S(O)$_m$ or O, m is 0 and n is 1; R$_3$ and R$_9$ are H or one or more of R$_3$ and R$_9$ are independently selected from H or C$_{1-2}$ alkyl; R$_2$, R$_8$ forms a C=C bond in an aromatic thiazole or oxazole ring; or
(C) when W$_3$ is S(O)$_m$, m is 0, and n is 1 or 2; R$_2$, R$_3$, R$_8$ and R$_9$ are H or one or more of R$_2$, R$_3$, R$_8$ and R$_9$ are independently selected from H or C$_{1-2}$ alkyl.

The term "Formula (If)" refers a compound represented by the structure:

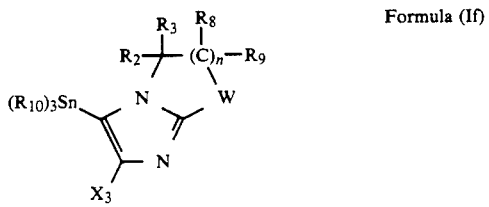

Formula (If)

wherein:
W is —CR$_5$=CR$_7$—, —N=CR$_7$—, —S— or —O—;
X$_3$ is (a) monosubstituted phenyl wherein said substituent is selected from C$_{1-3}$ alkylthio, C$_{1-2}$ alkoxy, halo, —H, or C$_{1-4}$ alkyl; or
(b) disubstituted phenyl wherein said substitutents are independently selected from C$_{1-3}$ alkylthio, C$_{1-2}$ alkoxy, halo, C$_{1-4}$ alkyl, or the disubstituents together form a methylene dioxy group;
provided that:
(1.) when W is —CR$_5$=CR$_7$— or —N=CR$_7$— then n is 1;
R$_3$, R$_5$, R$_7$ and R$_9$ are, independently, —H or C$_{1-2}$ alkyl;
R$_2$ and R$_8$ together represent a double bond in the B ring such that the B ring is an aromatic pyridine or pyrimidine ring; and
(2.) when W is —S— or —O— then
n is 1;
R$_3$ and R$_9$ are, independently, —H or C$_{1-2}$ alkyl; and
R$_2$ and R$_8$ are, independently, —H or C$_{1-2}$ alkyl or together represent a double bond in the B ring such that the B ring is an aromatic thiazole or oxazole ring;

The compounds of Formula (IA) can be prepared according to the following scheme:

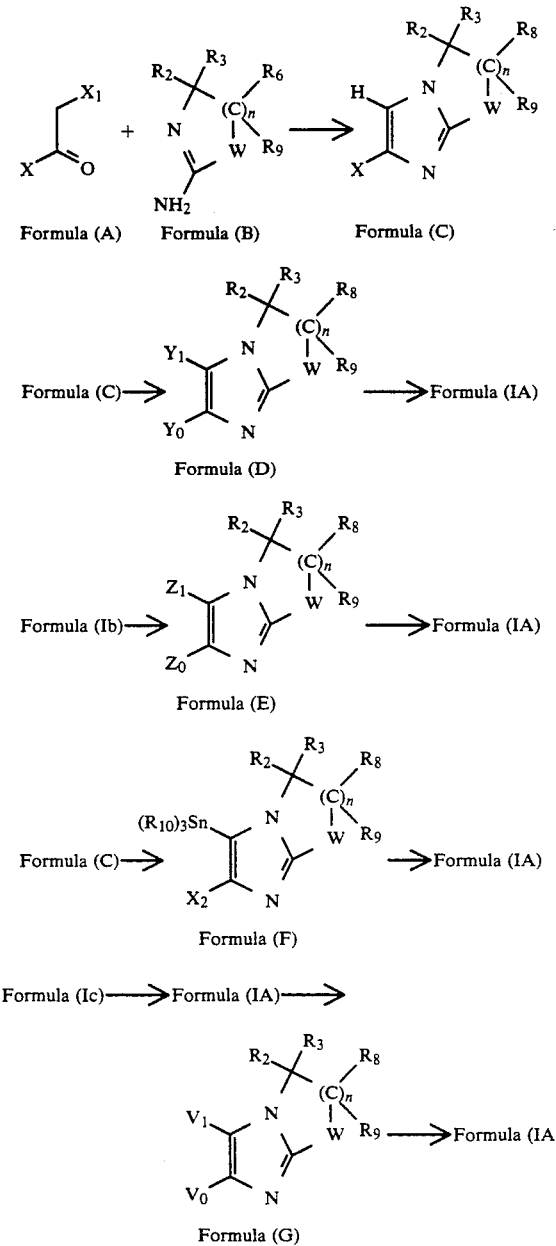

All the necessary 1-aryl-2-halo-ethanone Formula (A) compounds wherein $X_1$ is a halogen such as Cl or Br and X is chosen from a group consisting of mono or disubstituted phenyl, 4-pyridyl, and alkyl-substituted 4-pyridyl, are known in the art or are prepared by treatment of the correspondingly substituted 1-phenyl-ethanones or 1-(4-pyridyl)ethanones (which are commercially available or known in the art) with one equivalent of halogen, preferably bromine, in acetic acid, 48% hydrobromic acid, or a halocarbon solvent such as chloroform. See, e.g., Langley, *Org. Syn. Coll.*, 1, 127 (1944) and Taurins et al., *J. Heterocyclic Chem.*, 7, 1137 (1970). Alternatively, the mono and disubstituted 1-phenyl-2-chloro-ethanone Formula (A) compounds can be prepared by Friedel Crafts acylation of the corresponding mono or disubstituted benzenes with 2-chloroacetyl chloride and aluminum chloride by the method of Joshi et al., *J. Heterocyclic Chem.*, 16, 1141 (1979). By these methods, Formula (A) compounds are prepared wherein X is 4-pyridyl, mono-$C_{1-4}$alkyl-substituted pyridyl or monosubstituted phenyl (wherein said substituent is selected from $C_{1-3}$ alkylthio, $C_{1-2}$ alkoxy, halo, H, or $C_{1-4}$ alkyl); or disubstituted phenyl (wherein said substitutents are independently selected from $C_{1-3}$ alkylthio, $C_{1-2}$ alkoxy, halo or $C_{1-4}$ alkyl; or the disubstituents together form a methylene dioxy group).

Compounds of Formula (C) as defined above are prepared from the following classes of Formula (B) compounds wherein $R_2, R_3, R_4, R_5, R_6, R_7, R_8$ or $R_9$ are hydrogen or are one or more $C_{1-2}$ alkyl groups; i.e.,:

1. 2-amino-(1,3)-oxazole (W=O);
2. 2-amino-4,5-dihydro-(1,3)-thiazole (W=S, n=1);
3. 2-amino-5,6-dihydro-[4H]-(1,3)-thiazine (W=S, n=2);
4. 2-amino-(1,3)-thiazole (W=S, n=1, $R_2, R_8$ together represent a C=C bond);
5. 2-aminopyridine (W=C($R_4R_5$)—C($R_6R_7$)—, n=1; $R_2, R_8$ and $R_4, R_6$ together represent two C=C bonds); and
6. 2-aminopyrimidine (W=(N$R_4$)—(C$R_6R_7$)—, n=1; $R_2, R_8$ and $R_4, R_6$ together represent two C=C bonds).

The necessary Formula (B) compounds are commercially available or are known in the art and can be readily prepared by one of skill in the art.

The Formula (B) compound is reacted with a 1-aryl-2-halo-ethanone Formula (A) compound to afford the Formula (C) compound by alkylation followed by cyclodehydration. In this way, the following classes of Formula (C) compounds are prepared:

1. imidazo[2,1-b]oxazole (W=O, n=1, $R_2, R_8$ together represent a C=C bond);
2. 2,3-dihydroimidazo[2,1-b]thiazole (W=S, n=1); 3. 6,7-dihydro[5H]imidazo[2,1-b][1,3]thiazine (W=S, n=2);
4. imidazo[2,1-b]thiazole (W=S, n=1, $R_2, R_8$ together represent a C=C bond);
5. imidazo[1,2-a]pyridine (W=C($R_4R_5$)—C($R_6R_7$)—, n=1; $R_2, R_8$ and $R_4, R_6$ together represent two C=C bonds); and
6. imidazo[1,2-a]pyrimidine (W=(N$R_4$)—(C$R_6R_7$)—, n=1; $R_2, R_8$ and $R_4, R_6$ together represent two C=C bonds).

The reaction to form the Formula (C) compounds is performed in a nonpolar solvent such as chloroform or toluene, or in a polar nonprotic solvent such as dimethylformamide or acetonitrille. Alkylation is facilitated by the presence of one to four equivalents of a base such as powdered sodium carbonate or triethylamine, and cyclodehydration is facilitated by heating (between ambient temperature and reflux) or removing the solvent and refluxing the residue in water or dilute aqueous acid.

Compounds of Formula (D) as defined above are N-(substituted carbonyl)-1,4-dihydropyridines. The Formula (D) compounds are prepared by treatment of the corresponding Formula (C) compounds of classes 1, 4, 5 and 6 described above wherein X is selected from (a) monosubstituted phenyl (wherein said substituent is selected from $C_{1-3}$ alkylthio, $C_{1-2}$ alkoxy, halo, H, or $C_{1-4}$ alkyl); or (b) disubstituted phenyl (wherein said substitutents are independently selected from $C_{1-3}$ alkylthio, $C_{1-2}$ alkoxy, halo, $C_{1-4}$ alkyl, or the disubstituents together form a methylene dioxy group); or the corresponding Formula (C) compounds of classes 2 and 3 described above wherein X is disubstituted phenyl wherein said substitutents are selected from one of the following combinations: di($C_{1-3}$ alkylthio); dihalo($C_{1-3}$ alkylthio) and $C_{1-2}$ alkoxy; $C_{1-3}$ alkylthio and halo; $C_{1-3}$ alkylthio and $C_{1-4}$ alkyl; or $C_{1-2}$ alkoxy and halo; with a substituted carbonyl pyridinium salt by the method of Bender et al., U.S. Pat. No. 4,803,279, issued Feb. 9, 1989, and Adams et al., U.S. patent application Ser. No. 07/255,816, filed Oct. 11, 1988. The pyridinium salt may be either preformed or preferably prepared in situ by addition of the substituted carbonyl halide (such as an acyl halide, an aroyl halide, an arylalkyl haloformate ester, or preferably an alkyl haloformate ester) to a solution of the Formula (C) compound in pyridine or in an inert solvent such as methylene chloride to which pyridine has been added.

Compounds of Formula (C) may be treated with an alkyllithium compound to yield the corresponding lithium reagent by metanation. The lithium intermediate may then be treated with an excess of magnesium halide or zinc halide etherate to yield the corresponding organometallic reagent by transmetallation. To this organometallic reagent a 4-bromo, 4-iodopyridine or the triflate ester of a 4-hydroxy pyridine (a 4-trifluoromethylsulfonyloxypyridine) in the presence of a palladium (0) catalyst, such as tetrakis(triphenylphosphine)-palladium, with hexamethylphosphoramide; or a palladium (II) catalyst in the presence of lithium chloride and a base, such as sodium bicarbonate or triethylamine, to yield the corresponding Formula (IA) compounds. [See Kumada et al., *Tetrahedron Letters*, 22, 5319 (1981).]

One may also treat the litho derivatives of Formula (C) compounds, as prepared above, with a tirialkyltin halide, such as n-butyl tin chloride, to yield the intermediate compound represented herein as Formula (If). The compounds of Formula (If) may be utilized to produce the compounds of Formula (IA) wherein either $R_1$ or $R_0$ is a 4-pyridyl or mono alkylsubstituted pyridyl derivative or as a substituted phenyl. When the compounds of Formula (If) are reacted with a 4-pyridyl halide, preferably iodide, or the triflate ester of a hydroxy 4-pyridyl compound and tetrakis(triphenylphosphine)-palladium in a mixture of tetrahydrofuran and hexamethylphosphoramide or a mixture of the halide or triflate with a palladium (II) catalyst in the presence of lithium chloride and base.

The compounds of Formula (C) may also be treated with an excess of bromine to yield a 3-bromo derivative, wherein the substituent group of the phenyl on a Formula (C) compound is substituted with other than a bromine or iodinine, as a halogen substitutent group. To the bromo derivative of Formula (C) is added a pyridine boronic acid [B(OH)$_2$-4-pyridyl] with a palladium catalyst such as Pd(Ph$_2$P(CH$_2$)$_4$—PPh$_2$)Cl$_2$ or Pd(PPh$_3$)$_4$ in the presence of about three equivalents of sodium bicarbonate for about 12 hours in reflux conditions with a DME(dimethyl ethane)/H$_2$ in a 3:1 ratio. The pyridine-4-boronic acid is prepared from 4-bromopyridine by reaction with n-butyllithium, trapping of the anion with triethyl borate and acid hydrolysis of the boronate ester. The method is similar to that of Fischer and Haviniga, *Rec. Trav. Chim. pays Bas*, 84, 439 (1965). Additional references for coupling of bromopyridines with boronic acids are Sniechus, V., *Tetrahedron Lett.*, 29, 2135 (1988) and Terashimia, M., *Chem. Pharm. Bull.*, 11, 4755 (1985).

The brominated Formula (C) compound can also, following halogen-metal exchange with n-BuLi be coupled to a substituted halobenzene, preferably an iodide in the presence of bidentate palladium (II) catalyst or a Ni(II)Cl$_2$(1,2-bi-diphenyl-phosphino)ethane) catalyst to yield the desired regioisomer of the compounds of Formula (IA). [See, Pridgen, *J. Org. Chem.*, 47, 4319 (1982)]. The compounds of Formula (C) may be reacted in the above manner by treatment directly with a $C_{1-5}$alkyllithium compound to yield the corresponding lithium reagent by metallation and then proceed with the coupling reaction.

The lithio derivative of a Formula (C) compound, however derived, when X is other than a 4-mono $C_{1-4}$ alkylpyridyl or 4-pyridyl may be coupled to to a substituted 4-halopyridine in the presence of the noted palladium (II) or Ni(II) catalyst to yield the final desired compounds of Formula (IA).

Compounds of Formula (E) as defined above serve as intermediates in the preparation of Formula (IA) compounds where one of $R_0$ or $R_1$ in the product Formula (IA) compound is monoalkyl substituted pyridyl. Compounds of Formula (E) are N-(substituted carbonyl)-4-(1,2-dihydro-2-alkyl)pyridines and are prepared by the method of Comins et al., *J. Org. Chem.*, 47, 4315 (1982), i.e., by treatment of an appropriate Formula (Ib) compound in a dry ethereal solvent such as tetrahydrofuran at reduced temperature (below 0° C.) with a substituted carbonyl halide (such as an acyl halide, an aroyl halide, an arylalkyl haloformate ester, or preferably an alkyl haloformate ester), followed by treatment with an alkyl grignard reagent.

Formula (Ib) compounds where $W_2$ is $S(O)_m$, m is 0, n is 1 or 2; $R_2$, $R_3$, $R_8$ and $R_9$ are H or one or more of $R_2$, $R_3$, $R_8$ and $R_9$ are independently selected from H or $C_{1-2}$ alkyl; one of $R_1$ or $R_0$ is selected from 4-pyridyl and the other is selected from: (a) monosubstituted phenyl wherein said substituent is selected from $C_{1-3}$ alkylthio, $C_{1-2}$ alkoxy, halo, H, or $C_{1-4}$ alkyl; or (b) disubstituted phenyl wherein said substitutents are independently selected from $C_{1-2}$ alkoxy, $C_{1-4}$ alkyl; or (c) the disubstituents together form a methylene dioxy group; are prepared as described in Bender et al., U.S. Pat. No. 4,175,127, issued Nov. 20, 1979; Bender et al., U.S. patent application Ser. No. 07/106,199 filed on Jul. 10, 1987; or Bender et al., U.S. Pat. No. 4,803,279, issued Feb. 9, 1989.

The remaining Formula (Ib) compounds, i.e., those where (A) when $W_2$ is —(CR$_4$R$_5$)—(CR$_6$R$_7$)—, or —(NR$_4$)—(CR$_6$R$_7$)— and n is 1; $R_2$, $R_8$ and $R_4$, $R_6$ together represent two C≡C bonds to form an aromatic pyridine ring or an aromatic pyrimidine ring; $R_3$, $R_5$, $R_7$ and $R_9$ are H or one or more of $R_3$, $R_5$, $R_7$ and $R_9$ are independently selected from H or $C_{1-2}$ alkyl; or (B) when $W_2$ is $S(O)_m$ or O, m is 0 and n is 1; $R_3$ and $R_9$ are H or one or more of $R_3$ and $R_9$ are independently selected from H or $C_{1-2}$ alkyl; $R_2$, $R_8$ forms a C≡C bond in an aromatic thiazole or oxazole ring; and one of $R_1$ or $R_0$ is 4-pyridyl and the other is selected from (a) monosubstituted phenyl wherein said substituent is selected from $C_{1-3}$ alkylthio, $C_{1-2}$ alkoxy, halo, H, or $C_{1-4}$ alkyl; or (b) disubstituted phenyl wherein said substitutents are independently selected from $C_{1-3}$ alkylthio, $C_{1-2}$ alkoxy, halo, $C_{1-4}$ alkyl, or the disubstituents together form a methylene dioxy group; or (C) when $W_2$ is $S(O)_m$, m is O, and n is 1 or 2; $R_2$, $R_3$, $R_8$ and $R_9$ are H or one or more of $R_2$, $R_3$, $R_8$ and $R_9$ are independently selected from H or $C_{1-2}$ alkyl; and one of $R_1$ or $R_0$ is 4- pyridyl and the other is selected from disubstituted phenyl (wherein said substitutents are selected from one of the following combinations: di($C_1$-

3 alkylthio), dihalo, ($C_{1-3}$ alkylthio) and $C_{1-2}$ alkoxy, $C_{1-3}$ alkylthio and halo, $C_{1-3}$ alkylthio and $C_{1-4}$ alkyl, or $C_{1-2}$ alkoxy and halo),
are all embraced by the scope of Formula (IA) compounds and are obtained from intermediates of Formula (D) and Formula (F) compounds as more elaborately described herein.

Compounds of Formula (D) and Formula (E) are converted into compounds of Formula (IA) by deacylation and oxidation with a mild oxidizing agent by the methods described in Bender U.S. Pat. No. 4,803,279 and Adams et al., U.S. patent application Ser. No. 07/255,816, filed Oct. 11, 1988. Exemplary oxidation systems are sulfur in a refluxing inert solvent, or solvent mixture (such as decalin, decalin and diglyme, p-cymene, mesitylene), or oxygen in the presence of potassium tert.-butoxide/tert.-butanol.

Compounds of Formula (F) as defined above are intermediates to the corresponding Formula (IA) compounds and are prepared by metanation of the appropriate Formula (C) compounds, where X is 4-pyridyl or monoalkyl-substituted 4-pyridyl, with a lithiating agent (such as s-butyllithium or n-butyllithium) in an ethereal solvent (such as tetrahydrofuran), followed by treatment with a trialkyltin halide. These Formula (F) compounds are employed to prepare the Formula (IA) compounds where $R_0$ is 4-pyridyl or monoalkyl-substituted 4-pyridyl, i.e., one mole equivalent of the Formula (F) compound is added to an excess of a solution of a mono- or di-substituted phenyl bromide, triflate, or preferably the iodide, in an inert solvent (such as tetrahydrofuran) preferably containing 10% hexamethylphosphoramide and 1 to 10 mole percent of a palladium (0) catalyst (such as tetrakis(niphenylphosphine)palladium) by the method described in Adams et al., U.S. patent application Ser. No. 07/255,816, filed Oct. 11, 1988, or by using a palladium (n) catalyst in the presence of lithium chloride and an added base such as triethylamine. Triflate precursors are prepared from the corresponding substituted phenols by treatment with trifluorosulfonic anhydride in the presence of a base such as pyridine or triethylamine. Formula (F) compounds where W is $S(O)_m$, m is 0, n is 1 or 2, and $X_2$ is 4-pyridyl, are treated with a disubstituted phenyl bromide, triflate or preferably the iodide, wherein the substituents are selected from one of the following combinations: di($C_{1-3}$ alkylthio), dihalo, $C_{1-3}$ alkylthio and $C_{1-2}$ alkoxy, $C_{1-3}$ alkylthio and halo, $C_{1-3}$ alkylthio and $C_{1-4}$ alkyl, or $C_{1-2}$ alkoxy and halo. The remaining Formula (F) compounds are treated with (a) a monosubstituted phenyl bromide, triflate or preferably the iodide wherein said substituent is selected from $C_{1-3}$ alkylthio, $C_{1-2}$ alkoxy, halo, H, or $C_{1-4}$ alkyl; or (b) a disubstituted phenyl bromide, triflate or preferably the iodide wherein said substituents are independently selected from $C_{1-3}$ alkylthio, $C_{1-2}$ alkoxy, halo, $C_{1-4}$ alkyl, or the disubstituents together form a methylene dioxy group. Refluxing this mixture for 8 to 48 hours gives the desired Formula (IA) compounds after treatment with aqueous sodium fluoride solution.

The compounds of Formula (IA) wherein $R_1$ is a 4-pyridyl or $C_{1-4}$ alkyl-4-pyridyl may also be produced through use of a tin containing intermediate referred to herein as a Formula (If) compound. The same reaction conditions and methods apply for use of a Formula (If) compound as with a Formula (F) compound. A mixture of a 4-pyridyl halide, preferably iodide, or trifilate ester of a hydroxy 4-pyridyl compound and tetrakis (triphenylphosphine)-palladium in a mixture of tetrahydrofuran and hexamethylphosphoramide, or a palladium (II) catalyst in the presence of lithium chloride and a base, followed by optional hydrolysis, oxidation, or reduction to yield the desired compound of Formula (IA).

Compounds of Formula (IA) where one of $R_1$ or $R_0$ is mono or disubstituted phenyl possessing one or more 1-acyloxyalkylthio substituent(s) and compounds of Formula (G) (defined above) are prepared via Rummerer Rearrangement on the corresponding compounds of Formula (Ic). Pummerer Rearrangement of the corresponding Formula (Ic) compounds is accomplished by the method described in Adams et al., U.S. patent application Ser. No. 07/255,816, filed Oct. 11, 1988 by refluxing with an alkanoic acid anhydride.

The Formula (Ic) compounds wherein $W_3$ is $S(O)_m$, m is 0, n is 1 or 2; $R_2$, $R_3$, $R_8$ and $R_9$ are independently selected from H or $C_{1-2}$ alkyl; one of $R_1$ or $R_0$ is 4-pyridyl or mono-$C_{1-4}$alkyl- substituted-4-pyridyl, and the other of $R_1$ or $R_0$ is monosubstituted phenyl where said substituent is $C_{1-3}$ alkylsulfinyl are prepared by the method described in Bender et al., U.S. Pat. No. 4,175,127, issued Nov. 20, 1979, Bender et al., U.S. patent application. Ser. No. 07/106,199 filed on Jul. 10, 1987 or Bender et al., U.S. Pat. No. 4,803,279, issued Feb. 9, 1989.

The remaining Formula (Ic) compounds, i.e., those compounds of Formula (Ic) wherein (A) when $W_3$ is $-(CR_4R_5)-(CR_6R_7)-$ or $-(NR_4)-(CR_6R_7)-$ and n is 1; $R_2$, $R_8$ and $R_4$, $R_6$ together represent two C=C bonds to form an aromatic pyridine ring or an aromatic pyrimidine ring; $R_3$, $R_5$, $R_7$ and $R_9$ are H or one or more of $R_3$, $R_5$, $R_7$ and $R_9$ are independently selected from H or $C_{1-2}$ alkyl; or (B) when $W_3$ is $S(O)_m$ or O, m is 0 and n is 1; $R_3$ and $R_9$ are H or one or more of $R_3$ and $R_9$ are independently selected from H or $C_{1-2}$ alkyl; $R_2$, $R_8$ forms a C=C bond in an aromatic thiazole or oxazole ring; and one of $R_1$ or $R_0$ is 4-pyridyl or mono-$C_{1-4}$alkyl-substituted-4-pyridyl; and the other is selected from: (a) monosubstituted phenyl wherein said substituent is $C_{1-3}$ alkylsulfinyl; or (b) disubstituted phenyl wherein one of said substituents must by $C_{1-3}$ alkylsulfinyl and the other is selected from $C_{1-3}$ alkylsulfinyl, $C_{1-2}$ alkoxy, halo, or $C_{1-4}$ alkyl; or (c) when $W_3$ is $S(O)_m$, m is O, and n is 1 or 2; $R_2$, $R_3$, $R_8$ and $R_9$ are H or one or more of $R_2$, $R_3$, $R_8$ and $R_9$ are independently selected from H or $C_{1-2}$ alkyl; and one of $R_1$ or $R_0$ is 4-pyridyl or mono-$C_{1-4}$alkyl-substituted-4-pyridyl; the other is selected from disubstituted phenyl wherein one of said substituents must be $C_{1-3}$ alkylsulfinyl and the other is selected from $C_{1-3}$ alkylsulfinyl, $C_{1-2}$ alkoxy, halo, or $C_{1-4}$ alkyl; are all embraced by the scope of Formula (IA) and are prepared as described herein.

The Formula (G) compounds where one of $V_1$ or $V_0$ is mono or disubstituted phenyl having at least one mercapto substituent are obtained by hydrolysis of the Formula (IA) acyloxyalkylthio products or preferably by treatment of a Formula (Ic) compound with trifluoroacetic anhydride followed by basic solvolysis with a base such as sodium methoxide in methanol, similar to the method of R. N. Young et al., *Tetrahedron Letters*, 25, 1753 (1984).

Formula (G) compounds serve as intermediates for the synthesis of Formula (IA) compounds where one of $R_1$ or $R_0$ of the Formula (IA) compound is mono or disubstituted phenyl having at least one 2-alkenyl-1-thio function. A solution of the Formula (G) intermediate in a polar solvent such as dimethylformamide is treated with a strong base, such as a metal hydride, (preferably sodium hydride), a metal alkoxide or lithium diethylamide. The metal mercaptide salt is treated with a 1-halo-2-alkene such as allyl bromide and heated from 25° to 80° C. to give the Formula (IA) compounds where one of $R_1$ or $R_0$ is mono or disubstituted phenyl having at least one 2-alkenyl-1-thio substituent.

The Formula (G) compounds described above also serve as intermediates for the synthesis of Formula (IA) compounds in which one of $R_1$ or $R_0$ is mono or disubstituted phenyl having at least one 1-alkenyl-1-thio function. Treatment of the Formula (G) compound in a nonpretic solvent such as tetrahydrofuran with a strong base such as lithium diethylamide at low temperature ($-78°$ to $-20°$ C.) generates the lithium mercaptide salt. This salt is alkylated at 0° C. with a trimethylsilymethylating agent (such as trimethylsilymethyl halide, triflate, or acetate) to form the trimethylsilylmethylthio substituent. The latter is deprotonated with addition of another molar equivalent of lithium diethylamide and treated with an aldehyde or ketone to give the Formula (IA) compound where $V_0$ or $V_1$ is mono or disubstituted phenyl having one at least one 1-alkenyl-1-thio substituent.

Compounds of Formula (I) or (II) wherein R or $R^1$ is phenyl substituted with a substituted disulfide group are prepared by mild air oxidation of the compounds of Formula (I) wherein R or $R^1$ is phenyl substituted with a sulfhydryl group, prepared as described above. The nonsymmetrical disulfide (Z) wherein Z is S—S—$Z_1$ and $Z_1$ is phenyl or $C_{1-9}$ alkyl, the compound may be prepared by reaction of the sulfhydryl compound with the appropriate sulfenyl halide in an ethereal solvent to afford compounds of Formula (I) or (II) wherein one of R or $R^1$ is phenyl substituted with one or more alkyl-dithio or aryl-dithio groups The method of Mukaiyam et al., *Tetrahedron Letters*, 56:5907-08 (1968) allows for use of the desired aryl-SH or alkyl-SH reagent treated with diethylazodicarboxylate in 1:1 equivalence at room tempertaure in a solvent, yielding an adduct which is then treated with 1:1 ratio of the desired mercaptan of Formula (G). This process will also yield the disulfide dimer of the compounds of Formula (I) or (II).

Compounds of Formula (IA) where one of $R_1$ or $R_0$ is mono or disubstituted phenyl possessing a 4-halogen substituent (preferably fluoride) can be converted to the 4-alkylthio Formula (IA) compound by displacement of the halide ion with a metal alkyl-mercaptide salt (such as sodium thioethoxide) in a polar nonprotic solvent (such as dimethylformamide) heated to between 70° and 150° C. In compounds of Formula (IA) where W is $S(O)_m$ and the substituents $R_2,R_3,R_8,R_9$ are H or $C_{1-2}$ alkyl, m is preferably 0 for this conversion.

The Formula (G) compounds may be obtained by treatment of a halophenyl, preferably a fluro or bromo-phenyl derivative of a Formula (IA) or (Ib) compound having at least one halo substituent on the phenyl ring, in dimethyl sulfoxide (DMSO) with NaSH(sodium bisulfide) under similar conditions as formation of the Formula (IA) compounds as described above, with a metal mercaptide salt only for a longer temperature and time. A possible reaction to yield a Formula (C) or (IA) compound is to treat a halophenyl derivative of Formula (IA), (I]B) or (C) with the sodium salt of an alkyl-mercaptan with catalytic amount of a palladium (0) compound, such as tetrakis(triphenylphosphine)-palladium in a solvent, such as DMS. In the instance wherein the resulting Formula (IA) compound contains an alkylthiophenyl substituent, said compound may be oxidized in accordance with procedures well known to those skilled in the art, and as illustrated below for the Formula (IC) compounds, may then be used as an intermediate to make the mercapto compound of Formula (G).

Compounds of Formula (IA) or (IC) possessing an alkylsulfinyl, 1-alkenyl-1-sulfinyl, or 2-alkenyl-1-sulfinyl mono or disubstituted phenyl ring, or those compounds of Formula (IA) where W is S(O), are prepared by oxidation of the corresponding compounds of Formula (IA) or (IC) (possessing, respectively, an alkylthio, 1-alkenyl-1-thio or 2-alkenyl-1-thio mono or disubstituted phenyl ring or those compounds of Formula (IA) where W is S $(O)_m$ and m is 0), by employing one equivalent of oxidizing agent per sulfide in the molecule. The oxidizing agent may be an organic peracid (such as 3-chloroperoxybenzoic) added dropwise to a solution of the Formula (IA) or (IB) compound in a halocarbon (such as methylene chloride) at ice bath temperature, or an inorganic agent (such as sodium periodate or hydrogen peroxide) in water added dropwise to a solution of the Formula (IA) or (IC) compound in water containing 2 equivalents of an inorganic acid (such as hydrochloric acid) at ice bath temperature. Treatment of compounds of Formula (IA) containing two sulfide functions with one equivalent of oxidant results in the formation of a mixture of the sulfoxides.

Compounds of Formula (IA) where W is $S(O)_2$ are prepared by oxidation of the corresponding compounds of Formula (IA) where W is S(O) and is the only sulfoxide function in the molecule. The oxidation is achieved according to the method of Chatterway et al., *J. Chem. Soc.*, 1352 (1930), by dropwise addition of an aqueous solution of ⅔ equivalent of potassium permanganate per sulfoxide substituent to a solution of the Formula (IA) compound in water containing two equivalents of an inorganic acid such as hydrochloric acid. Ibis oxidation is selective for sulfoxides and allows the preparation of compounds of Formula (IA) where R or $R_1$ is mono or disubstituted alkylthiophenyl and W is $SO_2$.

EXAMPLE 1

6-(4-Fluorophenyl)-5-(4-(2-methyl)pyridyl)-2,3-dihydroimidazo- [2,1-b]thiazole Formula (IA) Compound a)
5-(4-(1-acetyl-2-methyl)-1,2-dihydropyridyl)-6-(4-fluorophenyl)-2,3-dihydroimidazo[2,1-b]thiazole (Formula (E) Compound A sniffed solution of 3.54 g (11.9 mmol) of 6-(4-fluorophenyl)-5-(4-pyridyl)-2,3-dihydroimidazo[2,1-b]-thiazole, prepared as disclosed in Bender et al., U.S. Pat. No. 4,803,279, in dry tetrahydrofuran (THF) cooled between 0° and $-50°$ C. is treated sequentially with 1.84 g (23.8 mmol) of acetyl chloride and subsequently with 8.81 mL (23.8 mmol) of 2.7M methyl magnesium bromide. The reaction mixture is allowed to come to 25° C., quenched with saturated $NH_4Cl$, adjusted to pH 7.5 with 10% sodium bicarbonate and extracted with methylene chloride. The combined organic extract is dried, concentrated in vacuo and flash chromatographed on silica to afford the title Formula (E) compound in a semi-stable form.

b)
6-(4-Fluorophenyl)-5-(4-(2-methyl)pyridyl)-2,3-dihydroimidazo[2,1-b]thiazole

Formula (IA) Compound
Method A

The 1-acetyl-1,2-dihydropyridine derivative of part a, above is aromatized by heating between 165° and 195° C. with 1.0 g (31 mmol) of sublimed sulfur in a solution of 10% diglyme in decalin until thin layer chromatography (e.g., alumina, methylene chloride) shows the starting material is consumed. The reaction mixture is filtered warm, and extracted into dilute aqueous HCl. The aqueous acid phase is neutralized with 5% aqueous sodium carbonate and extracted into methylene chloride. This extract is dried, concentrated in vacuo and purified by flash chromatography on silica to afford the title Formula (IA) compound.

Method B

The 1-acetyl-1,2-dihydropyridine derivative of part a, above is aromatized by adding to a stirred solution of 2.7 to 8.0 g (24–71 mmoles) of potassium t-butoxide dissolved in sieve dried t-butanol into which oxygen is being bubbled. The solution is heated to reflux until thin layer chromatography (alumina, methylene chloride) shows the starting material is consumed. The solvent is removed in vacuo, and the residue is partitioned between 5% aqueous sodium carbonate and methylene chloride. The organic phase is washed with water and extracted into dilute aqueous HCl. The acidic aqueous phase is made alkaline with aqueous sodium carbonate and extracted into methylene chloride. The organic layer is dried over anhydrous sodium carbonate, stripped in vacuo and the residue chromatographed on silica to afford the title Formula (IA) compound.

EXAMPLE 2

6-(4-Methylthiophenyl)-5-(4-(2-methyl)pyridyl)-2,3-dihydroimidazo[2,1-b]thiazole Formula (IA) Compound
Method A A stirred solution of 6.13 g (19.7 mmoles) of 6-(4-fluorophenyl)-5-(4-(2-methyl)pyridyl)-2,3-dihydroimidazo[2,1-b]thiazole, prepared as described in Example 1b, in dry dimethylformamide (DMF) is treated with 1.65 g (23.6 mmoles) of sodium thiomethoxide under argon atmosphere and the reaction mixture heated between 75° and 140° C. until the starring material has been consumed. The mixture is then cooled, poured into cold water and extracted with ethyl acetate. The organic phase is washed three times with water, dried over anhydrous sodium sulfate and stripped in vacuo. The residue is chromatographed on silica to afford the title Formula (IA) compound.

Method B

The title compound is prepared by treatment of 6-(4-methylthiophenyl)-5-(4-pyridyl)-2,3-dihydroimidazo[2,1-b]thiazole, prepared as disclosed in Bender et al., U.S. Pat. No. 4,803,279, by the methods of Example 1a and 1b.

EXAMPLE 3

6-(4-Fluorophenyl)-5-(4-(2-methyl)pyridyl)-2,3-dihydroimidazo-[2,1-b]thiazole-1-oxide Formula (IA) Compound
A stirred solution of 5.08 g (16.3 mmoles) of 6-(4-fluorophenyl)-5-(4-(2-methyl)pyridyl)-2,3-dihydroimidazo[2,1-b]thiazole, prepared as described in Example 1b, dissolved in chloroform is chilled in an ice bath and treated dropwise with a solution of 3.30 g (16.3 mmoles) of 85% 3-chloroperbenzoic acid in chloroform. The solution is stirred at 25° C. overnight and then is washed with 5% aqueous sodium carbonate, dried over anhydrous potassium carbonate, and stripped in vacuo. The residue is chromatographed on silica and recrystallized to give the title compound.

EXAMPLE 4

6-(4-Methylthiophenyl)-5-(4-(2-methyl)pyridyl)-2,3-dihydroimidazo[2,1-b]thiazole-1-oxide Formula (IA) Compound (Method A)

The title compound is prepared by treatment of 6-(4-fluorophenyl)-5-(4-(2-methyl)pyridyl)-2,3-dihydroimidazo- [2,1-b]thiazole-1-oxide, prepared as described in Example, 3, according to the procedure of Example 2.

Method B

The title compound is also prepared as described in Example 6 below.

EXAMPLE 5

6-(4-Methylthiophenyl)-5-(4-(2-methyl)pyridyl)-2,3-dihydroimidazo[2,1-b]thiazole-1,1-dioxide Formula (IA) Compound A stirred mixture of 3.41 g (9.6 mmoles) of 6-(4-methylthiophenyl)-5-(4-(2-methyl)pyridyl)-2,3-dihydroimidazo[2,1-b]thiazole-1-oxide, prepared as described in Example 4, in water containing 1.95 g of concentrated hydrochloric acid is treated dropwise with a solution of 1.01 g (6.38 mmoles) of potassium permanganate dissolved in water. The reaction mixture is neutralized with 5% aqueous sodium hydroxide solution. The crude product is extracted into methylene chloride, washed with water, dried over anhydrous sodium sulfate and stripped in vacuo. The residue is chromatographed on silica to give the title compound.

EXAMPLE 6

6-(4-Methylsulfinylphenyl)-5-(4-(2-methyl)pyridyl)-2,3-dihydroimidazo[2,1-b]thiazole Formula (IA) compound A mixture of 0.38 g (1.12 mmoles) of 6-(4-methylthiophenyl)-5-(4-(2-methyl)pyridyl)-2,3-dihydroimidazo[2,1-b]thiazole, prepared as described in Example 2, in water containing 0.75 ml of 3 N hydrochloric acid is treated dropwise at 5° C. with a solution of 0.241 g (1.12 mmoles) of sodium periodate in water. The reaction mixture is kept at this temperature overnight and then is warmed to 20° C. and washed with methylene chloride. The aqueous phase is brought to pH 10 with sodium carbonate, and the crude product is extracted into methylene chloride. The organic phase is dried over anhydrous potassium carbonate, and stripped in vacuo to give a product mixture. This residue is flash chromatographed on silica and the two sulfoxides isolated to give both the title compound as well as 6-(4-methylthiophenyl)-5-(4-(2-methyl)pyridyl)-2,3-dihydroimidazo[2,1-b]thiazole-1-oxide Formula (IA) compound of Example 4.

EXAMPLE 7

6-(4-Methylsulfinylphenyl)-5-(4-(2-methyl)pyridyl)-2,3-dihydroimidazo[2,1-b]thiazole-1,1-dioxide Formula (IA) Compound The title compound is prepared by submitting 6-(4-methylthiophenyl)-5-(4-(2-methyl)pyridyl)-2,3-dihydroimidazo[2,1-b]thiazole-1, 1 -dioxide, prepared as described in Example 5, to the procedure of Example 6.

EXAMPLE 8

6-(4-Mercaptophenyl)-5-(4-(2-methyl)pyridyl)-2,3-dihydroimidazo[2,1-b]thiazole (Formula (G) Compound.

A solution of 5.51 g (15.5 mmoles) of 6-(4-methylsulfinylphenyl)-5-(4-(2-methyl)pyridyl)-2,3-dihydroimidazo[2,1-b]thiazole, prepared as described in Example 6, in methylene chloride cooled to 0° C. is treated with 9.7 g (46.4 mmoles, 6.5 ml) of trifluoroacetic anhydride in methylene chloride. The mixture is heated to reflux for 1 hour and stripped in vacuo. The residue is treated with water and extracted into methylene chloride. The organic phase is washed with aqueous sodium bicarbonate, saturated brine, dried over anhydrous sodium sulfate and stripped in vacuo. A solution of this residue in anhydrous methanol is treated with 5 ml (23 mmoles) of a 25% solution of sodium methoxide in methanol and stirred at room temperature for 3 hours. This solution is then poured into ice-water, treated with 3N sodium bicarbonate solution, and concentrated in vacuo to remove most of the methanol. This mixture is then extracted into methylene chloride, and the organic phase is washed with water, saturated brine, dried over anhydrous sodium sulfate and stripped in vacuo. The residue is chromatographed on silica to afford the title compound.

EXAMPLE 9

6-(4-(2-Methyl-1-propenylthio)phenyl)-5-(4-(2-methyl)pyridyl)-2,3-dihydroimidazo[2,1-b]thiazole Formula (IA) Compound A solution of 5.53 g (17 mmoles) of 6-(4-mercaptophenyl)-5-(4-(2-methyl)pyridyl)-2,3-dihydroimidazo(2,1-b]thiazole, prepared as described in Example 8, in dry tetrahydrofuran at −20° C. under an argon atmosphere is treated with a solution of 17 mmoles of lithium diethylamide from 6.8 ml of 2.5M n-butyl lithium. After warming, a solution of 1.57 g (17 mmoles) of trimethylsilylmethyl chloride in dry tetrahydrofuran is added dropwise. When the reaction is complete, the mixture is immersed in an ice-bath and a second 17 mmole solution of lithium diethylamide is added. After stirring for 15 minutes, a solution of 0.99 g (17 mmoles) of dry acetone in tetrahydrofuran is added and the reaction allowed to come to room temperature. The mixture is poured into water, extracted with methylene chloride and the organic phase dried over sodium sulfate and stripped in vacuo. The residue is chromatographed on silica to afford the title compound.

EXAMPLE 10

2-(4-Methoxyphenyl)-3-(4-pyridyl)imidazo[1,2-a]2pyridine

Formula (IA) Compound a) 2-(4-Methoxyphenyl)imidazo[1,2-a]pyridine (Formula (C) Compound)

A chloroform solution of 7.3 g (32 mmoles) of 1-(4-methoxyphenyl)-2-bromo-ethan-1-one and 3.0 g (32 mmoles) of 2-aminopyridine was stirred for 5 hours and a precipitate was obtained on chilling. This precipitate was washed with cold carbon tetrachloride and recrystallized from ethyl acetate to afford the title compound, melting point (mp) 135°–137° C., Calcd for $C_{14}H_{12}N_2O$; C: 74.98; H: 5.39, N: 12.49, Found, C: 74.64, H: 5.35, N: 12.63.

b) 2-(4-Methoxyphenyl)-3-(l-ethoxycarbonyl-1,4-dihydropyridylimidazo[1,2-a]pyridine (Formula (D) Compound).

A solution of 1.5 g (6.69 mmoles) of 2-(4-methoxyphenyl)imidazo[1,2-a]pyridine, prepared as described in Example 10a, dissolved in 20 mi of dry methylene chloride containing 5.29 g (66.9 mmoles) of pyridine was treated with 3.63 g (33.4 mmoles) of ethyl chloroforrnate over one hour. After 72 hours, the mixture was poured into 0.3N HCl at 0° C. and extracted into methylene chloride. The organic phase was washed with 0.3N HCl, water and then dried over anhydrous sodium sulfate. The solvent was stripped in vacuo to give the title compound as a tan powder, $^1$H-NMR 250 MHz, $CDCl_3$) o 8.17 (d,1 H), 7.60 (d,1 H), 7.50 (d,2 H), 7.12 (d-d,1 H), 7.0 (br s,2 H), 6.92 (d,2 H), 6.76 (t,1 H), 5.02 (p,l H), 4.79 (br s,2 H), 4.32 (q,2 H), 3.7 6 (s,3 H), 1.3 0 (t,3 H).

c) 2-(4-Methoxyphenyl)-3-(4-pyridyl)imidazo[1,2-a]pyridine

Formula (IA) Compound.

A mixture of 1.2 g (3.20 mmoles) of 2-(4-methoxyphenyl)-3-(1-ethoxycarbonyl-1,4-dihydropyridyl)-imidazo[1,2-a]pyridine, prepared as described in Example 10b, in 10 ml of decalin was heated at 185° to 190° C. under argon with 0. 154 g (4.8 mmoles) of sublimed sulfur for 1.5 hours. The cooled reaction mixture was extracted with 3N HCl and the aqueous layer washed with methylene chloride, made alkaline with 5% sodium carbonate solution and extracted with methylene chloride. The basic organic phase was dried over anhydrous potassium carbonate and stripped i-n vacuo. The residue was chromatographed on silica and eluted with 1 to 8% of methanol in chloroform/ethyl acetate (1:1). Recrystallization two times from ethyl acetate/ether and once from ethyl acetate/hexane gave the title compound, mp 127.5°–128.5° C., Calcd for $C_{19}H_{15}N_3O$; C: 75.73, H: 5.02, N: 13.94; found C: 75.96, H: 5.05, N: 14.00.

EXAMPLE 11

2-(4-Fluorophenyl)-3-(4-pyridyl)imidazo[1,2-a]pyridine

Formula (IA) Compound a) 2-(4-Fluorophenyl)imidazo[1.2-a]pyridine (Formula (C) Compound)

1-(4-Fluorophenyl)-2-bromo-1-ethanone is reacted by the method of Example 10a, and such reaction is followed by evaporation of the solvent and reflux of the crude product in water or dilute aqueous HCl. The mixture is treated with 5% aqueous sodium carbonate and extracted with methylene chloride. The organic phase is dried and evaporated to give the title compound.

b) 2-(4-Fluorophenyl)-3-(4-pyridyl)imidazo[1,2-a]pyridine

Formula (IA) Compound

The tide compound is prepared by treating 2-(4-fluorophenyl)imidazo[1,2-a]pyridine, prepared as described in Example 11a, according to the method of Example 10b and 10c.

EXAMPLE 12

2-(4-Methylthiolthiophenyl)-3-(4-pyridyl)imidazo[1,2-a]pyridine

Formula (IA) Compound

The title compound is prepared by treating 2-(4-Fluorophenyl)-3-(4-pyridyl)imidazo[1,2-a]pyridine, prepared as described in Example 11, according to the method of Example 2.

EXAMPLE 13

2-(4-Methylsulfinylphenyl)-3-(4-pyridyl)imidazo[1,2-a]pyridine

Formula (IA) Compound

The title compound is prepared by treating 2-(4-methylthiophenyl)-3-(4-pyridyl)imidazo[1,2-a]pyridine, prepared as described in Example 12, according to the method of Example 6.

EXAMPLE 14

2-(4-Acetoxymethylthiophenyl)-3-(4-pyridyl)imidazo[1,2-a]pyridine

Formula (IA) Compound

To 1 g (2.7 mmoles) of 2-(4-methylsulfinylphenyl)-3-(4-pyridyl)imidazo[1,2-a]pyridine, prepared as described in Example 13, is added 25 ml of acetic anhydride, and the mixture is heated to reflux for one hour. After cooling, the mixture is stripped in vacuo, treated with water and extracted with methylene chloride. The organic phase is washed with 3N sodium bicarbonate and saturated aqueous sodium chloride solution, dried over sodium sulfate and stripped in vacuo. The residue is chromatographed on silica to give the title compound.

EXAMPLE 15

2-(4-Mercaptophenyl)-3-(4-pyridyl)imidazo[1,2-a]pyridine

Formula (G) Compound

The tide compound is prepared by treating 2-(4-methylsulfinylphenyl)-3-(4-pyridyl)imidazo[1,2-a]-pyridine, prepared as described in Example 13, according to the method of Example 8.

EXAMPLE 16

2-(4-(2-propenyl-1-thio)phenyl)-3-(4-pyridyl-imidazo[1,2-a]pyridine

Formula (IA) Compound

A solution of 0.5 g (1.65 mmoles) of 2-(4-mercaptophenyl)-3-(4-pyridyl)imidazo[1,2-a]pyridine, prepared as described in Example 15, in dry dimethylformamide under an argon atmosphere is treated with 0.079 g (1.98 mmoles) of 60% sodium hydride and stirred at room temperature for one hour. A solution of 0.24 g (1.98 mmoles) of 2-propenyl bromide in dimethylfonnamide is then added dropwise and heated between 25 and 65° C. until the reaction is complete. The mixture is then poured into ice water and extracted three times with ethyl acetate. The organic phase is washed three times with water, dried over anhydrous potassium carbonate and concentrated in vacuo. The residue is chromatographed on silica to afford the title compound.

EXAMPLE 17

2-(4-Pyridyl)-3-(4-methylsulfinyl)phenyl)imidazo[1,2-a]pyridine

Formula (IA) Compound a) 2-(4-Pyridyl)imidazo[1,2-a]pyridine (Formula (C) Compound A stirred suspension of 1.0 g (3.6 mmoles) of 4-(bromoacetyl)pyridine hydrobromide and 1.02 g (10.8 mmoles) of 2-aminopyridine in dry dimethylformamide is treated with 0.76 g (7.2 mmoles) of powdered anhydrous sodium carbonate and heated between 35° and 100° C. under an argon atmosphere until no further product forms. The solvent is removed in vacuo and the residue is dissolved in water. The aqueous mixture is extracted with chloroform and the organic phase washed with water, dried over anhydrous potassium carbonate and stripped in vacuo. The residue is chromatographed on silica to afford the title compound.

b) 2-(4-Pyridyl)-3-(imidazo[1,2-a]pyridyl)-tri-n-butyltin (Formula (F) Compound).

A cold (−20° to −5° C.) solution of 0.53 g (2.7 mmoles) of 2-(4-pyridyl)imidazo[1,2-a]pyridine, prepared as described in Example 17a, in dry tetrahydrofuran under an argon atmosphere is treated dropwise with 1.08 ml (2.7 mmoles) of a 2.5M solution of n-butyllithium in hexane over 20 minutes. The reaction mixture is stirred until all the starting material is lithiated and then a solution of 1.0 g (3.07 mmoles) of tri-n-butyltin chloride in dry tetrahydrofuran is added dropwise. After sniffing for one hour, the mixture is treated with a saturated aqueous solution of ammonium chloride. The organic layer is washed again with aqueous ammonium chloride and dried over anhydrous potassium carbonate. The solvent is stripped in vacuo and the residue extracted with hexane and chromatographed on silica with solvent containing 1% diethylamine. Removing the solvent in vacuo affords the title compound.

c) 2-(4-Pyridyl)-3-(4-methylthiophenyl)imidazo[1,2-a]pyridine

Formula (IA) Compound

A solution of 2.69 g (10.9 mmoles) of 1-methylthio-4-iodobenzene in dry tetrahydrofuran containing 10% hexamethylphosphoramide is purged by bubbling with argon for several minutes and then treated with 240 mg of tetrakis(triphenylphosphene)palladium. The mixture was heated at 50° C. for several minutes and then treated with a solution of 1.73 g (3.57 mmoles) of 2-(4-pyridyl)-3-(imidazo[1,2-a]pyridyl)-tri-n-butyltin, prepared as described in Example 17b above, in dry tetrahydrofuran. The mixture is refluxed until all the tin compound is gone, then it is cooled, ethyl acetate is added, and the mixture is washed with 10% aqueous sodium fluoride solution, three times with water and extracted into cold dilute HCl. The aqueous phase is washed with methylene chloride, made alkaline with 10% sodium hydroxide, and the product extracted into methylene chloride. The organic phase is dried over anhydrous potassium carbonate, stripped in vacuo and the residue chromatographed on silica to afford the title compound.

d) 2-(4-Pyridyl)-3-(4-methylsulfinyl)phenyl)imidazor[1,2-a]]pyridine

Formula (IA) Compound

The title compound is prepared by treating 2-(4-pyridyl)-3-(4-methylthiophenyl)imidazo[1,2-a]pyridine, prepared as described in Example 17c, according to the method of Example 6.

EXAMPLE 18

6-(4-Fluorophenyl)-5-(4-pyridyl)imidazo[2,1-b]thiazole

Formula (IA) Compound

The title compound is prepared by treating 2-aminothiazole by the method of Example 11a and 11b.

EXAMPLE 19

6-(4-Methylthiophenyl)-5-(4-pyridyl)imidazo[2,1-b]thiazole

Formula (IA) Compound

The title compound is prepared by treating 6-(4-Fluorophenyl)-5-(4-pyridyl)-imidazo[2,1-b]thiazole, prepared as described in Example 18, according to the method of Example 2.

EXAMPLE 20

6-(4-Methylsulfinylphenyi)-5-(4-pyridyl)imidazo[2,1-b]thiazole

Formula (IA) Compound

The title compound is prepared by treating 6-(4-methylthiophenyl)-5-(4-pyridyl)imidazo[2,1-b]thiazole, prepared as described in Example 19, according to the method of Example 6.

EXAMPLE 21

6-(4-Fluorophenyl)-5-(4-pyridyl)imidazo[2,1-b]oxazole

Formula (IA) Compound

The title compound is prepared by treating 2-aminooxazole according to the method of Example 11a and 11b.

EXAMPLE 22

6-(4-Methylthiophenyl)-5-(4-pyridyl)imidazo[2,1-b]oxazole

Formula (IA) Compound

The title compound is prepared by treating 6-(4-Fluorophenyl)-5-(4-pyridyl)imidazo[2,1-b]oxazole, prepared as described in Example 21, according to the method of Example 2.

EXAMPLE 23

6-(4-Methylsulfinylphenyl)-5-(4-pyridyl)imidazo[2,1-b]oxazole

Formula (IA) Compound

The title compound is prepared by treating 6-(4-methylthiophenyl)-5-(4-pyridyl)-imidazo[2,1-b]oxazole, prepared as described in Example 22, according to the method of Example 6.

EXAMPLE 24

2-(4-Fluorophenyl)-3-(4-pyridyl)imidazo[1,2-a]pyrimidine

Formula (IA) Compound a) 2-(4-Fluorophenyl)imidazo[1,2-a]pyrimidine

Formula (C) Compound)

The title compound is prepared by treating 2-aminopyrimidine according to the method of Example 11a and 11b.

b) 2-(4-Fluorophenyl)-3-(4-pyridyl)imidazo[1,2-a]pyrimidine

Formula (IA) Compound

The title compound is prepared by treating 2-(4-fluorophenyl)-imidazo[1,2-a]pyrimidine, prepared as described in Example 24a, according to the method of Example 10b and 10c.

EXAMPLE 25

2-(4-Methylthiophenyl)-3-(4-pyridyl)imidazo[1,2-a]pyrimidine

Formula (IA) Compound

The title compound is prepared by treating 2-(4-Fluorophenyl)-3-(4-pyridyl)-imidazo[1,2-a]pyrimidine, prepared as described in Example 24, according to the method of Example 2.

EXAMPLE 26

2-(4-Methylsulfinylphenyl)-3-(4-pyridyl)imidazo[1,2-a]pyrimidine

Formula (IA) Compound

The title compound is prepared by treating 2-(4-methylthiophenyl)-3-(4-pyridyl)-imidazo[1,2-a]-pyrimidine, prepared as described in Example 25, according to the method of Example 6.

EXAMPLE 27

2-(4-Methylthiophenyl)-3-(4-pyridyl)-6,7-dihydro[5-H]imidazo[2,1-b][1,3-thiazine Formula (IA) Compound The title compound is prepared by treating 2-(4-fluorophenyl)-3-(4-pyridyl)-6,7-dihydro[5H]imidazo-[2,1-b][1,3]thiazine, prepared as disclosed in Bender et al., U.S. Pat. No. 4,803,279, according to the method of Example 2.

Formula (IA) Compound

The title compound is prepared by treating 2-(4-methylthiophenyl)-3-(4-pyridyl)-6,7-dihydro[5-H]imidazo-[2,1-b][1,3]thiazine, prepared as described in Example 27 above according to the method of Example 6.

The above description fully discloses the invention including preferred embodiments thereof Modifications and improvements of the embodiments specifically disclosed herein are within the scope of the following claims. Without further elaboration, it is believed that one skilled in the art can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows.

What is claimed is:

1. A method of inhibiting the production of interleukin-1 (IL-1) by monocytes and/or macrophages in a human in need thereof which comprises administering to such human an effective, IL-1 production inhibiting amount of a compound of the formula

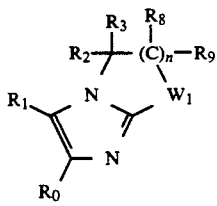

FORMULA (I)

wherein:
$W_1$ is $-(CR_4R_5)-(CR_6R_7)-$, $-CR_5=CR_7-$, $-N=CR_7-$, $-S(O)_m-$ or $-O-$;
n is 0 to 2;
one of $R_1$ and $R_0$ is 4-pyridyl or $C_{1-4}$ alkyl-4-pyridyl, provided that when $R_1$ is $C_{1-4}$ alkyl-4-pyridyl the alkyl substituent is located at the 2-position of the pyridine ring, and the other of $R_1$ and $R_0$ is
(a) phenyl or monosubstituted phenyl wherein said substituent is $C_{1-3}$ alkylthio, $C_{1-3}$ alkylsulfinyl, $C_{2-5}$ 1-alkenyl-1-thio, $C_{2-5}$ 1-alkenyl-1-sulfinyl, $C_{3-5}$ 2-alkenyl-1-thio, $C_{3-5}$ 2-alkenyl-1-sulfinyl, 1-acyloxy-1-alkylthio, $C_{1-4}$ alkyl or Z wherein Z is $-S-S-Z_1$ and $Z_1$ is phenyl or $C_{1-9}$ alkyl; or
(b) disubstituted phenyl wherein said substituents are, independently, $C_{1-3}$ alkylthio or $C_{1-4}$ alkyl; or
(c) disubstituted phenyl wherein one of said substituents is $C_{1-3}$ alkylsulfinyl, $C_{2-5}$ 1-alkenyl-1-thio, $C_{2-5}$ 1-alkenyl-1-sulfinyl, $C_{3-5}$ 2-alkenyl-1-thio, $C_{3-5}$ 2-alkenyl-1-sulfinyl or 1-acyloxy-1-alkylthio and the other is $C_{1-2}$ alkoxy, halo, or $C_{1-4}$ alkyl;
(d) disubstituted phenyl wherein the substituents are the same and are $C_{1-3}$ alkylsulfinyl, $C_{2-5}$ 1-alkenyl-1-thio, $C_{2-5}$ 1-alkenyl-1-sulfinyl, $C_{3-5}$ 2-alkenyl-1-thio, $C_{3-5}$ 2-alkenyl-1-sulfinyl or 1-acyloxy-1-alkylthio; or
(e) monosubstituted phenyl wherein the substituent is

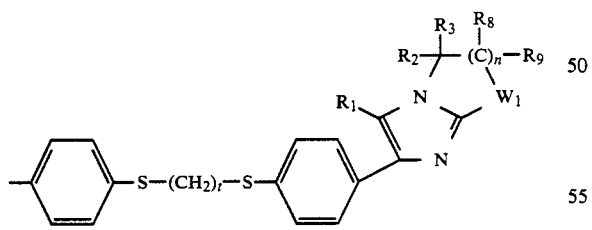

t is 0 or 1; $W_1$ and $R_1$ are as defined above;
provided that:
(1.) when $W_1$ is $-(CR_4R_5)-(CR_6R_7)-$ then
n is 0 or 1; and
$R_2$, $R_3$, $R_4$, $R_5$, $R_6$, $R_7$, $R_8$, and $R_9$ are, independently, $-H$ or $C_{1-2}$ alkyl; or
when n is 0, $R_4$ and $R_5$ together form an oxo; $R_4$ and $R_5$ may both be fluoro, or one of $R_4$ and $R_5$ is H and the other is OH; or
(2.) when $W_1$ is $-CR_5=CR_7-$ or $-N=CR_7-$ then
n is 1;

$R_3$, $R_5$, $R_7$ and $R_9$ are, independently, $-H$ or $C_{1-2}$ alkyl; and
$R_2$ and $R_8$ together represent a double bond in the B ring such that the B ring is an aromatic pyridine or pyrimidine ring;
(3.) when $W_1$ is $S(O)_m$ then
m is 0, 1 or 2;
n is 1 or 2; and
$R_3$ and $R_9$ are, independently, $-H$ or $C_{1-2}$ alkyl;
$R_2$ and $R_8$ are, independently, $-H$ or $C_{1-2}$ alkyl or $R_2$ and $R_8$ together represent a double bond in the B ring such that the B ring is an aromatic thiazole ring and
m is 0 and n is 1; and
(4) when $W_1$ is $-O-$ then
n is 1;
$R_3$ and $R_9$ are, independently, $-H$ or $C_{1-2}$ alkyl; and
$R_2$ and $R_8$ together represent a double bond in the B ring such that the B ring is an aromatic oxazole ring;
or a pharmaceutically acceptable salt thereof.

2. The method of claim 1 wherein:
$W_1$ is $-(CR_4R_5)-(CR_6R_7)-$, $-CR_5=CR_7-$, or $-S(O)_m-$;
one of $R_1$ and $R_0$ is 4-pyridyl or $C_{1-2}$ alkyl-4-pyridyl, provided that when $R_1$ is $C_{1-2}$ alkyl-4-pyridyl the alkyl substituent is located at the 2-position of the pyridine ring, and the other of $R_1$ and $R_0$ is
(a) monosubstituted phenyl wherein said substituent is $C_{1-2}$ alkylthio, $C_{1-3}$ alkylsulfinyl, 1-acyloxy-1-alkylthio; or
(b) disubstituted phenyl wherein said substituents are, independently, $C_{1-2}$ alkylthio, or
(c) disubstituted phenyl wherein one of said substituents is $C_{1-2}$ alkylsulfinyl or 1-acyloxy-1-alkylthio and the other is $C_{1-2}$ alkoxy, or
(d) disubstituted phenyl wherein the substituents are the same and are $C_{1-2}$ alkylsulfinyl or 1-acyloxy-1-alkylthio;
provided that:
(1.) when $W_1$ is $-(CR_4R_5)-(CR_6R_7)-$ then
n is 0 or 1; and
$R_2$, $R_3$, $R_4$, $R_5$, $R_6$, $R_7$, $R_8$, and $R_9$ are $-H$; or
when n is 0, $R_4$ and $R_5$ together form an oxo; $R_4$ and $R_5$ may both be fluoro, or one of $R_4$ and $R_5$ is H and the other is OH; or
(2) when $W_1$ is $-CR_5=CR_7-$ then
n is 1;
$R_3$, $R_5$, $R_7$ and $R_9$ are $-H$; and
$R_2$ and $R_8$ together represent a double bond in the B ring such that the B ring is an aromatic pyridine ring;
(3.) when $W_1$ is $S(O)_m$ then
m is 0, 1 or 2;
n is 1 or 2; and
$R_3$ and $R_9$ are $-H$;
$R_2$ and $R_8$ are $-H$ or $R_2$ and $R_8$ together represent a double bond in the B ring such that the B ring is an aromatic thiazole ring and m is 0 and n is 1; and
(4) when $W_1$ is $-O-$ then
n is 1;
$R_3$ and $R_9$ are $-H$; and
$R_2$ and $R_8$ together represent a double bond in the B ring such that the B ring is an aromatic oxazole ring;
or a pharmaceutically acceptable salt thereof.

3. The method of claim 2 wherein the compound is 2-(4-methylthiophenyl)-3-(4-pyridyl)-6,7-dihydro-[5H]-pyrrolo[1,2-a]imidazole;

2-(4-methylsulfinylphenyl)-3-(4-pyridyl)-6,7-dihydro-[5H]-pyrrolo[1,2-a]imidazole;

2-(4-ethylthiophenyl)-3-(4-pyridyl)-6,7-dihydro-[5H]-pyrrolo[1,2-a]imidazole;

2-(4-ethylsulfinylphenyl)-3-(3-pyridyl)-6,7-dihydro-[5H]-pyrrolo[1,2-a]imidazole;

2-(4-methylthiophenyl)-3-(4-(2-methyl)pyridyl)-6,7-dihydro-[5H]-pyrrolo[1,2-a]imidazole;

2-(4-methylsulfinylphenyl)-3-(4-(2-methyl)pyridyl)-6,7-dihydro-[5H]-pyrrolo[1,2a-]-imidazole;

2-(4-acetoxymethylthiophenyl)-3-(4-pyridyl)-6,7-dihydro-[5H]-pyrrolo[1,2-a]imidazole;

2-(trimethylacetylthiophenyl)-3-(4-pyridyl)-6,7-dihydro-[5H]-pyrrolo[1,2-a]imidazole;

6-(4-methylthiophenyl)-5-(4-pyridyl)-2,3-dihydro-imidazo-[2,1-b]thiazole;

5-(4-methylthiophenyl)-6-(4-pyridyl)-2,3-dihydro-imidazo-[2,1-b]thiazole;

3-(4-methylthiophenyl)-2-(4-pyridyl)-6,7-dihydro-[5H]-pyrrolo[1,2-a]imidzole;

2-(4-propylthiophenyl)-3-(4-pyridyl)-6,7-dihydro-[5H]-pyrrolo[1,2-a]-imidazole;

2-(4-methylthiophenyl)-3-(4-(2-ethyl)pyridyl)6,7-dihydro-[5H]-pyrrolo-[1,2-a]-imidazole;

2-(4-Mercaptophenyl)-3-(4-pyridyl)-6,7-dihydro-[5H]-pyrrolo[1,2-a]-imidazole disulfide;

or a pharmaceutically acceptable salt of any one of the above compounds.

4. The method of claims 1 to 3 wherein the route of administration is parenteral, oral, topical, or by inhalation.

* * * * *